US007528164B2

(12) United States Patent
Cai et al.

(10) Patent No.: US 7,528,164 B2
(45) Date of Patent: May 5, 2009

(54) SUBSTITUTED 4-ARYL-4H-PYRROLO[2,3-H]CHROMENES AND ANALOGS AS ACTIVATORS OF CASPASES AND INDUCERS OF APOPTOSIS AND THE USE THEREOF

(75) Inventors: Sui Xiong Cai, San Diego, CA (US); Songchun Jiang, San Diego, CA (US); William E. Kemnitzer, San Diego, CA (US); Hong Zhang, San Diego, CA (US); Giorgio Attardo, Laval (CA); Real Denis, Montreal (CA)

(73) Assignees: Cytovia, Inc., San Diego, CA (US); Shire BioChem, Inc., Quebec (CA)

( * ) Notice: Subject to any disclaimer, the term of this patent is extended or adjusted under 35 U.S.C. 154(b) by 294 days.

(21) Appl. No.: 10/514,427

(22) PCT Filed: May 16, 2003

(86) PCT No.: PCT/US03/15427

§ 371 (c)(1),
(2), (4) Date: Nov. 16, 2004

(87) PCT Pub. No.: WO03/097806

PCT Pub. Date: Nov. 27, 2003

(65) Prior Publication Data

US 2006/0104998 A1    May 18, 2006

Related U.S. Application Data

(60) Provisional application No. 60/378,079, filed on May 16, 2002.

(51) Int. Cl.
    *A61K 31/407* (2006.01)
(52) U.S. Cl. .................. 514/411; 548/430
(58) Field of Classification Search ............. 548/430;
    514/411
    See application file for complete search history.

(56) References Cited

U.S. PATENT DOCUMENTS

| 4,303,656 | A | 12/1981 | Sime et al. |
| 4,698,345 | A | 10/1987 | Dicker et al. |
| 5,281,619 | A | 1/1994 | Dell et al. |
| 5,284,868 | A | 2/1994 | Dell et al. |
| 5,434,160 | A | 7/1995 | Dell et al. |
| 5,514,706 | A | 5/1996 | Ambler et al. |
| 5,571,818 | A | 11/1996 | Williams |
| 5,574,034 | A | 11/1996 | Williams |
| 5,576,325 | A | 11/1996 | Williams |
| 5,624,953 | A | 4/1997 | Ambler et al. |
| 5,637,589 | A | 6/1997 | Lee et al. |
| 5,726,204 | A | 3/1998 | Lee et al. |
| 5,741,818 | A | 4/1998 | Dimmock |
| 5,847,165 | A | 12/1998 | Lee et al. |
| 5,902,792 | A | 5/1999 | Jayaram |
| 5,994,390 | A | 11/1999 | Jacobsen et al. |
| 6,160,010 | A | 12/2000 | Uckun et al. |
| 6,221,900 | B1 | 4/2001 | Uckun et al. |
| 6,258,824 | B1 | 7/2001 | Yang |
| 6,294,575 | B1 | 9/2001 | Uckun et al. |
| 6,303,652 | B1 | 10/2001 | Uckun et al. |
| 6,323,228 | B1 | 11/2001 | BaMaung et al. |
| 6,365,626 | B1 | 4/2002 | Uckun et al. |
| 6,388,092 | B2 | 5/2002 | Yang |
| 6,828,091 | B2 | 12/2004 | Kasibhatla et al. |
| 6,858,607 | B1 | 2/2005 | Cai et al. |
| 6,858,609 | B2 | 2/2005 | Janssen et al. |
| 6,906,203 | B1 | 6/2005 | Drewe et al. |
| 7,015,328 | B2 | 3/2006 | Cai et al. |
| 7,053,117 | B2 * | 5/2006 | Cai ..................... 514/456 |
| 2003/0065018 | A1 | 4/2003 | Cai et al. |
| 2005/0090526 | A1 | 4/2005 | Cai et al. |
| 2005/0154015 | A1 | 7/2005 | Drewe et al. |
| 2005/0165053 | A1 | 7/2005 | Cai et al. |
| 2005/0176750 | A1 | 8/2005 | Cai et al. |
| 2006/0035925 | A1 | 2/2006 | Cai et al. |
| 2006/0135505 | A1 * | 6/2006 | Tajimi et al. ......... 514/210.17 |

FOREIGN PATENT DOCUMENTS

EP        0 481 243 A1    4/1992

(Continued)

OTHER PUBLICATIONS

Dorwald F. A. Side Reactions in Organic Synthesis, 2005, Wiley: VCH, Weinheim p. IX of Preface.*
Zhang et. al. "Discovery and SAR of indole-2-carboxylic acid benzylidenehydrazides as a new series of potent apoptosis inducers using a cell based HTS assay." Bioorganic & Medicinal Chemistry 2004, 12, 3649-3655.*
Drewe et al. Bioorganic & Medicinal Chemistry Letters 2007, 17, 4987-4990.*
Sirisoma et al. Bioorganic & Medicinal Chemistry 2006, 14, 7761-7773.*
Wolff, Manfred E. "Burger's Medicinal Chemistry, 5ed, Part I", John Wiley & Sons, 1995, pp. 975-977.*

(Continued)

*Primary Examiner*—Janet L Andres
*Assistant Examiner*—David K O'Dell
(74) *Attorney, Agent, or Firm*—Sterne, Kessler, Goldstein & Fox, P.L.L.C.

(57) ABSTRACT

The present invention is directed to substituted 4H-chromenes and analogs thereof, represented by the Formula (I): wherein $R^1$, $R^3$-$R^5$, A, D, Y and Z are defined herein. The present invention also relates to the discovery that compounds having Formula (I) are activators of caspases and inducers of apoptosis. Therefore, the activators of caspases and inducers of apoptosis of this invention can be used to induce cell death in a variety of clinical conditions in which uncontrolled growth and spread of abnormal cells occurs.

22 Claims, No Drawings

FOREIGN PATENT DOCUMENTS

| | | |
|---|---|---|
| EP | 0 537 949 A1 | 4/1993 |
| EP | 0 599 514 A1 | 6/1994 |
| EP | 0 619 314 A1 | 10/1994 |
| EP | 0 618 206 B1 | 9/1997 |
| WO | WO 96/20721 A1 | 7/1996 |
| WO | WO 98/24427 A2 | 6/1998 |
| WO | WO 99/18856 A1 | 4/1999 |
| WO | WO 99/54286 A2 | 10/1999 |
| WO | WO 99/62510 A2 | 12/1999 |
| WO | WO 00/04901 A1 | 2/2000 |
| WO | WO 00/47574 A1 | 8/2000 |
| WO | WO 01/34591 A2 | 5/2001 |
| WO | WO 02/092076 A1 | 11/2002 |
| WO | WO 02/092083 A1 | 11/2002 |
| WO | WO 02/092594 A1 | 11/2002 |
| WO | WO 03/096982 A2 | 11/2003 |
| WO | WO 03/097806 A2 | 11/2003 |

OTHER PUBLICATIONS

Banker (Modern Pharmaceutics) Banker, G.S. et al, "Modern Pharmaceutics, 3ed.", Marcel Dekker, New York, 1996, pp. 451 and 596.*

Abstract of Elgamal, M.H.A, et al., "Synthesis of some novel nitrogenous furocoumarin derivatives," *Polish J. Chem.* 72:735-745, Polish Chemical Society (1998), Accession No. 128:321530 CA.

Abstract of El-Taweel, M.A.E.A., et al., "Synthesis of 4H-naphtho[2,1-b]pyrans, benzo [h]coumarins, 4H-naphtho[2,1-b:6.5-b]dipyrans 4H-naphto[1,2-b:3,4-b']dipyrans and pyridine derivatives," *Anales de Quimica* 91:589-593, Real Sociedad Espanola de Quimica (1995), Accession No. 125:114568 CA.

Abstract of European Patent No. EP 0 481 243, Meguro, K. et al., "Tricyclic heterocyclic compounds, their production and use," Accession No. 117:69733 CA.

Abstract of Radwan, A.M., et al., "A new route for the synthesis of 1,2,4-triazole and 3,4-disubsitiuted cinnoline derivatives," *J. Chem. Soc. Pakistan* 17:113-117, Chemical Society of Pakistan (1995), Accession No. 124:117193 CA.

Abstract of Tawada, H., et al., "Synthesis of 3-ureido derivatives of coumarin and 2-quinolone as potent acyl-CoA: cholesterol acyltransferase inhibitors," *Chem. Pharm. Bull.* 43:616-625, Pharmaceutical Society of Japan (1995), Accession No. 123:339669 CA.

Abstract of Woods, L.L. and Sterling, J., "New synthesis of naphtho[1,2-b]pyran-2-ones," *J. Org. Chem.* 29:502-504, American Chemical Society (1964), Accession No. 60:44584 CA.

Abstract of Al-Mousawa, S.M., et al., "Synthesis of New Condensed 2-Amino-4H-pyran-3-carbonitriles and of 2-Aminoquinoline-3-carbonitriles," *Organic Preparations and Procedures Int.* 31:305-313, Organic Preparations and Procedures, Inc. (1999), CAPLUS Accession No. 131:199593, 2 pages (1999).

Al-Mousawi, S.M., et al., "Synthesis of New Condensed 2-Amino-4H-pyran-3-carbonitriles and of 2-Aminoquinoline-3-carbonitriles," *Organic Preparations and Procedures Int.* 31:305-313, Organic Preparations and Procedures, Inc. (1999).

*Apoptosis and Cancer Chemotherapy*, Hickman, J.A. and Dive, C., eds., Humana Press, Totowa, NJ (1999), 4 pages (includes Title Page, Foreword, Preface, Contents and Contributors).

Batteux, F., et al., "Gene Therapy of Experimental Autoimmune Thyroiditis by In Vivo Administration of Plasmid DNA Coding for Fas Ligand," *J. Immunol.* 162:603-608, The American Association of Immunologists (1999).

Birch, K.A., et al., "LY290181, an Inhibitor of Diabetes-Induced Vascular Dysfunction, Blocks Protein Kinase C-Stimulated Transcriptional Activation Through Inhibition of Transcription Factor Binding to a Phorbol Response Element," *Diabetes* 45:642-650, American Diabetes Association (1996).

Bloxham, J., et al., "Preparation of Some New Benzylidenemalononitriles by an $S_NAr$ Reaction: Application to Naphtho[1,2-*b*]pyran Synthesis," *Heterocycles* 38:399-408, The Japanese Institute of Heterocyclic Chemistry (1994).

Boirivant, M., et al., "Lamina Propria T Cells in Crohn'n Disease and Other Gastrointestinal Inflammation Show Defective CD2 Pathway-Induced Apoptosis," *Gastroenterol.* 116:557-565, Elsevier, Inc. (1999).

Bremner, A.R.F. and Beattie, R.M., "Therapy of Crohn's disease in childhood," *Expert Opin. Pharmacother.* 3:809-825, Ashley Publications Ltd. (2002).

Chandrasekhar, S., et al., "Identification of a Novel Chemical Series That Blocks Interleukin-1-Stimulated Metalloprotease Activity in Chondrocytes," *J. Pharmacol. Exper. Ther.* 273:1519-1528, The American Society for Pharmacology and Experimental Therapeutics (1995).

Coven, T.R., et al., "PUV A-induced lymphocyte apoptosis: Mechanism of action in psoriasis," *Photoderm. Photoimmunol. Photomed.* 15:22-27, Munksgaard (1999).

Elagamey, A.G.A., et al., "Nitriles In Heterocyclic Synthesis: Novel Syntheses of Benzo[*b*]pyrans, Naphtho[1,2-*b*]pyrans, Naphtho[2,1-*b*]pyrans, Pyrano[3,2-*h*]quinolines and Pyrano [3,2-*c*]quinolines," *Collection Czechoslovak Chem. Commun.* 53:1534-1538, Czechoslovak Academy of Sciences (1988).

Elagamey, A.G.A. and El-Taweel, F.M.A.A., "Nitriles in heterocyclic synthesis: Synthesis of condensed pyrans," *Indian J. Chem.* 29B:885-886, The Council of Scientific & Industrial Research, New Delhi (1990).

Elgert, K.D., "Immunology—Understanding the Immune System," pp. 315-331, John Wiley & Sons, Inc. (1996).

Ellis, R.E., et al., "Mechanisms and Functions of Cell Death," *Ann. Rev. Cell Biol.* 7:663-698, Annual Reviews, Inc. (1991).

Friesen, C., et al., "Involvement of the CD95 (APO-1/Fas) receptor/ligand system in drug-induced apoptosis in leukemia cells," *Nat. Med.* 2:574-577, Nature Publishing Co. (1996).

Gourdeau, H., et al., "Antivascular and antitumor evaluation of 2-amino-4-(3-bromo-4,5-dimethoxy-phenyl)-3-cyano-4*H*-chromenes, a novel series of anticancer agents," *Mol. Cancer Ther.* 3:1375-1383, American Association for Cancer Research (Nov. 2004).

Greenwald, R.B., et al., "Drug Delivery Systems Employing 1,4- or 1,6-Elimination: Poly(ethylene glycol) Prodrugs of Amine-Containing Compounds," *J. Med. Chem.* 42:3657-3667, American Chemical Society (1999).

Heenen, M., et al., "Methotrexate induces apoptotic cell death in human keratinocytes," *Arch Dermatol. Res.* 290:240-245, Springer-Verlag (1998).

Infante, A.J., et al., "The clinical spectrum in a large kindred with autoimmune lymphoproliferative syndrome caused by a Fas mutation that impairs lymphocyte apoptosis," *J. Pediatr.* 133:629-633, Mosby, Inc. (1998).

Kasibhatla, S., et al., "Discovery and mechanism of action of a novel series of apoptosis inducers with potential vascular targeting activity," *Mol. Cancer Ther.* 3:1365-1373, American Association for Cancer Research (Nov. 2004).

Kemnitzer, W., et al., "Discovery of 4-Aryl-4*H*-chromenes as a New Series of Apoptosis Inducers Using a Cell- and Caspase-based High-Throughput Screening Assay. 1. Structure-Activity Relationships of the 4-Aryl Group," *J. Med. Chem.* 47: 6299-6310, American Chemical Society (Nov. 2004).

Kemnitzer, W. et al., "Discovery of 4-aryl-4*H*- chromenes as a new series of apoptosis inducers using a cell- and caspase-based high-throughput screening assay. 2. Structure-activity relationships of the 7- and 5-, 6-, 8-positions," *Bioorg. Med. Chem. Letts.* 15:4745-4751, Elsevier Ltd. (Sep. 2005).

Klokol, G.V., et al., "Cyclization of Nitriles. XXIII. Addition of Active Phenols to Electron-Deficient Ethylenes, Accompanied by Cyclization to 2-Amino-4H-benzo[b]pyrans. Crystal Structure of 2-Amino-4-(2-fluorophenyl)-3-ethoxycarbonyl-4H-naphtho[2,1-b]pyran," *J. Organic Chem. of USSR* 23:369-377, Plenum Publishing Corporation (1987).

Klokol, G.V., et al., "Cyclization of nitriles, XXIII. Addition of active phenols to electron-deficient ethylenes with cyclization to 2-amino-4H-benzo[b]pyrans. Crystal structure of 2-amino-4-(2-fluorophenyl)-3-(ethoxycarbonyl)4H-naphtho[2,1-b]pyran," *Chem. Abstr.* 108:5822c, Chemical Abstracts Service (1988).

Leu, Y.-L., et al., "Design and Synthesis of Water-Soluble Glucuronide Derivatives of Camptothecin for Cancer Prodrug Monotherapy and Antibody-Directed Enzyme Prodrug Therapy (ADEPT)," *J. Med. Chem.* 42:3623-3628, American Chemical Society (1999).

López-Hoyos, M., et al., "Regulation of B cell apoptosis by Bcl-2 and Bcl-$X_L$ and its role in the development of autoimmune diseases (Review)," *Intl. J. Mol. Med.* 1:475-483, D.A. Spandidos (1998).

Los, M., et al., "Cross-Resistance of CD95- and Drug-Induced Apoptosis as a Consequence of Deficient Activation of Capases (ICE/Ced-3 Proteases)," *Blood* 90:3118-3129, W.B. Saunders Company (1997).

Ohsako, S. and Elkon, K.B., "Apoptosis in the effector phase of autoimmune diabetes, multiple schlerosis and thyroiditis," *Cell Death Diff.* 6:13-21, Stockton Press (1999).

O'Reilly, L.A. and Strasser, A., "Apoptosis and autoimmune-disease," *Inflamm. Res.* 48:5-21, Birkhäuser Verlag, Basel (1999).

Orrenius, S., "Apoptosis: molecular mechanisms and implications for human disease," *J. Internal Med.* 237:529-536, Blackwell Science Ltd. (1995).

Ozawa, M., et al., "312-nanometer Ultraviolet B Light (Narrow-Band UVB) Induces Apoptosis of T-Cells within Psoriatic Lesions," *J. Exp. Med.* 189:711-718, The Rockefeller University Press (1999).

Panda, D., et al., "Suppression of Microtubule Dynamics by LY290181," *J. Biol. Chem.* 272:7681-7687, The American Society for Biochemistry and Molecular Biology, Inc. (1997).

Paull, K.D., et al., "Identification of Novel Antimitotic Agents Acting at the Tubulin Level by Computer-assisted Evaluation of Differential Cytotoxicity Data," *Can. Res.* 52:3892-3900, The American Association for Cancer Research. Inc. (1992).

Radwan, S.M., et al., "Synthesis and Some Reactions of New Benzo[*b*]pyran Derivatives," *Phosphorus, Sulfur, and Silicon* 101:207-211, Overseas Publishers Association (1995).

Ram, V.J. and Verma, M., "Synthesis of 4*H*-benzopyrans, benzopyrano[2,3-*d*]pyrimidines and related compounds as biodynamic agents," *Ind. J. Chem.* 33B:908-911, Publications & Information Directorate (CSIR) (1994).

Robinson, M., "Medical Therapy of Inflammatory Bowel Disease for the 21st Century," *Eur. J. Surg.* 164(Suppl. 582):90-98, Scandinavian University Press (1998).

Savill, J., "Apoptosis in resolution of inflammation," *J. Leukoc. Biol.* 61:375-380, Society for Leukocyte Biology (1997).

Schmitt, E., et al., "The Bcl-xL and Bax-α control points: modulation of apoptosis induced by cancer chemotherapy and relation to TPCK-sensitive protease and caspase activation," *Biochem. Cell Biol.* 75:301-314, National Research Council of Canada (1997).

Sen, S. and D'Incalci, M., "Apoptosis: Biochemical events and relevance to cancer chemotherapy," *FEBS* 307:122-127, Elsevier Science Publishers B.V. (1992).

Sharanin, Y.A. and Klokol, G.V., "Synthesis of 2-amino-4H-chromenes," *Chem. Abstr.* 99:212393z, Chemical Abstracts Service (1983).

Sharanin, Y.A. and Klokol, G. V., "Synthesis of 2-Amino-4H-chromenes," *J. Organic Chem. of USSR* 19:1582-1583, Plenum Publishing Corporation (1984).

Shevach, E.M., "Animal Models for Autoimmune and Inflammatory Disease," *Current Protocols in Immunology, Suppl.* 52:15.0.1-15.0.6, John Wiley & Sons, Inc. (2002).

Simone, J.V., "Oncology: Introduction," *Cecil Textbook of Medicine*, 20th Edition, Bennett, J.C. and Plum, F., eds., vol. 1, pp. 1004-1010, W.B. Saunders Company (1996).

Singh, B., et al., "Immune therapy in inflammatory bowl disease and models of colitis," *Brit. J. Surg.* 88:1558-1569, Blackwell Science Ltd. (2001).

Smith, C.W., et al., "The Anti-Rheumatic Potential of a Series of 2,4-Di-substituted-4H-naphtho[1,2-b]pyran-3-carbonitriles," *Biorg. Med. Chem. Lett.* 5:2783-2788, Elsevier Science Ltd. (1995).

Supplementary Partial European Search Report for European Patent Application No. 02741704.7, European Patent Office, The Hague, Netherlands, 6 pages, dated Aug. 30 , 2005.

Thornberry, N.A., et al., "A Combinatorial Approach Defines Specificities of Members of the Caspase Family and Granzyme B," *J. Biol. Chem.* 272:17907-17911, The American Society for Biochemistry and Molecular Biology, Inc. (1997).

Thornberry, N.A., "Caspases: key mediators of apoptosis," *Chem. Biol.* 5:R97-R103, Current Biology Ltd. (1998).

Thornberry, N.A., "The caspase family of cysteine proteases," *Brit. Med. Bull.* 53:478-490, Oxford University Press (1997).

Vaishnaw, A.K., et al., "The molecular basis for apoptotic defects in patients with CD95 (Fas/Apo-1) mutations," *J. Clin. Invest.* 103:355-363, American Society for Clinical Investigation (1999).

Wachlin, G., et al., "IL-1β, IFN-γ and TNF-α increase vulnerability of pancreatic beta cells to autoimmune destruction," *J. Autoimmunity* 20:303-312, Elsevier Science Ltd. (Jun. 2003).

Wakisaka, S., et al., "Modulation of proinflammatory cytokines of Fas/Fas ligand-mediated apoptotic cell death of synovial cells in patients with rheumatoid arthritis (RA)," *Clin. Exp. Immunol.* 114:119-128, Blackwell Science (1998).

Wiernicki, T.R., et al, "Inhibition of Vascular Smooth Muscle Cell Proliferation and Arterial Intimal Thickening by a Novel Antiproliferative Naphthopyran," *J. Pharmacol. Exper. Ther.* 278:1452-1459, The American Society for Pharmacology and Experimental Therapeutics (1996).

Wood, D.L., et al., "Inhibition of Mitosis and Microtubule Function through Direct Tubulin Binding by a Novel Antiproliferative Naphthopyran LY290181," *Mol. Pharmacol.* 52:437-444, Williams & Wilkins (1997).

Wyllie, A.H., "Cell death: a new classification separating apoptosis from necrosis," in *Cell death in biology and pathology*, Bowen, I.D. and Lockshin, R.A., eds., Chapman and Hall, London, pp. 9-34 (1981).

Wyllie, A.H., et al., "Cell Death: The Significance of Apoptosis," *Int. Rev. Cyt.* 68:251-306, Academic Press, Inc. (1980).

Zhou, T., et al., "Bisindolylmaleimide VIII facilitates Fas-mediated apoptosis and inhibits T cell-mediated autoimmune diseases," *Nature Med.* 5:42-48, Nature Publishing Group (1999).

International Search Report for International Application No. PCT/US03/15427, United States Patent Office, Alexandria, Virginia, mailed on Jun. 30 ,2004.

Prosecution history for Cai, S.X. et al., U.S. Appl. No. 10/146,138, filed May 16, 2002, now published as 2003/0065018 A1.

Prosecution history for Cai, S.X. et al., U.S. Appl. No. 10/146,139, filed May 16, 2002, now patented as 6,858,607 B1.

Prosecution history for Cai, S.X. et al., U.S. Appl. No. 10/146,136, filed May 16, 2002, now published as 2003/0114485 A1.

Prosecution history for Drewe, J.A. et al., U.S. Appl. No. 09/705,840, filed Nov. 6, 2000, now patented as 6,906,203 B1.

Office Action for U.S. Appl. No. 10/989,057, Cai, S.X., et al., filed Nov. 16, 2004, mailed Mar. 16, 2006.

Barinaga, M., "Cell Suicide: By Ice, not Fire," *Science* 263:754-756, American Association for the Advancement of Science (1994).

Bode, A. and Dong. Z., "Apoptosis induction by arsenic: mechanisms of action and possible clinical applications for treating therapy-resistant cancers," *Drug Resist. Update* 1:21-29, Harcourt Publishers Ltd. (2000).

Ding, Z., et al., "Resistance to apoptosis is correlated with the reduced caspase-3 activation and enhanced expression of antiapoptotic proteins in human cervical multidrug-resistant cells," *Biochem. Biophys. Res. Comm.* 270:415-420, Academic Press (2000).

Klokol, G.V. et al., Cyclization of Nitriles. XXIII. *J. Org. Chem. USSR* 23:369-377, Consultants Bureau (1987).

McCarty, M.F., "Polyphenol-mediated inhibition of AP-1 transactivating activity may slow cancer growth by impeding angiogenesis and tumor invasiveness," *Medical Hypotheses* 50:511-514, Churchill Livingstone. (1998).

Nørgaard, J.M. and Hokland, P., "Biology of Multiple Drug Resistance in Acute Leukemia," *Int. J. Hematol.* 72:290-297 (2000), erratum 73:132 (Jan. 2001) Carden Jennings (2000).

Ruddon, R.W., "Biochemistry of Cancer," in *Cancer Medicine*, 5th Ed., B.C. Decker Inc., London, GB, pp. 108-120 (2000).

Salvesen, G.S. and Dixit, V.M., "Caspase activation: The induced-proximity model," *Proc. Natl. Acad. Sci. USA* 96:10964-10967, National Academy of Sciences (1999).

Sharanin, Yu.A. and Klokol, G.V., "Synthesis of 2-Amino-4H-chromenes," *J.Org. Chem. USSR 19*: 1582-1583, Consultants Bureau (1983).

Wolfe, B.B. and Green, D.R., "Suicidal Tendencies: Apoptotic Cell Death by Caspase Family Proteinases," *J. Biol. Chem.* 274:20049-20052, The American Society for Biochemistry and Molecular Biology, Inc. (1999).

Robinson, Binta M., Office Action for U.S. Appl. No. 11/072,499, U.S. Patent and Trademark Office, Alexandria, Virginia, mailed Oct. 9, 2007.

* cited by examiner

SUBSTITUTED 4-ARYL-4H-PYRROLO[2,3-H]CHROMENES AND ANALOGS AS ACTIVATORS OF CASPASES AND INDUCERS OF APOPTOSIS AND THE USE THEREOF

BACKGROUND OF TH INVENTION

1. Field of the Invention

This invention is in the field of medicinal chemistry. In particular, the invention relates to substituted 4H-chromenes and analogs, and the discovery that these compounds are activators of caspases and inducers of apoptosis. The invention also relates to the use of these compounds as therapeutically effective anti-cancer agents.

2. Description of Related Art

Organisms eliminate unwanted cells by a process variously known as regulated cell death, programmed cell death, or apoptosis. Such cell death occurs as a normal aspect of animal development, as well as in tissue homeostasis and aging (Glucksmann, A., *Biol. Rev. Cambridge Philos. Soc.* 26:59-86 (1951); Glucksmann, A., *Archives de Biologie* 76:419-437 (1965); Ellis, et al., *Dev.* 112:591-603 (1991); Vaux, et al., *Cell* 76:777-779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237: 529-536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9-34). A cell activates its internally encoded suicide program as a result of either internal or external signals. The suicide program is executed through the activation of a carefully regulated genetic program (Wyllie, et al., *Int. Rev. Cyt.* 68:251 (1980); Elis, et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529-536 (1995).

It has been found that a group of proteases are a key element in apoptosis (see, e.g., Thornberry, *Chemistry and Biology* 5:R97-R103 (1998); Thornberry, *British Med. Bull.* 53:478-490 (1996)). Genetic studies in the nematode *Caenorhabditis elegans* revealed that apoptotic cell death involves at least 14 genes, 2 of which are the pro-apoptotic (death-promoting) ced (for cell death abnormal) genes, ced-3 and ced-4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (*Apoptosis and Cancer Chemotherapy*, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become immortal—they become cancerous. In the case of the apoptosis process, control points are known to exist that represent points for intervention leading to activation. These control points include the CED-9-BCL-like and CED-3-ICE-like gene family products, which are intrinsic proteins regulating the decision of a cell to survive or die and executing part of the cell death process itself; respectively (see, Schmitt, et al., *Biochem. Cell Biol.* 75:301-314 (1997)). BCL-like proteins include BCL-xL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los, et al., *Blood* 90:3118-3129 (1997); Friesen, et al., *Nat. Med.* 2:574 (1996)). The mechanism of action of current antineoplastic drugs frequently involves an attack at specific phases of the cell cycle. In brief, the cell cycle refers to the stages through which cells normally progress during their lifetime. Normally, cells exist in a resting phase termed $G_o$. During multiplication, cells progress to a stage in which DNA synthesis occurs, termed S. Later, cell division, or mitosis occurs, in a phase called M. Antineoplastic drugs, such as cytosine arabinoside, hydroxyurea, 6-mercaptopurine, and methotrexate are S phase specific, whereas antineoplastic drugs, such as vincristine, vinblastine, and paclitaxel are M phase specific. Many slow growing tumors, e.g., colon cancers, exist primarily in the $G_o$ phase, whereas rapidly proliferating normal tissues, e.g., bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (see, e.g., Hardman, et al., eds., *Goodman and Gilman's The Pharmacological Basis of Therapeutics*, Ninth Edition, McGraw-Hill, New York (1996), pp. 1225-1287). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducers of apoptosis is a highly desirable goal in the development of therapeutically effective antineoplastic agents. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

EP537949 discloses derivatives of 4H-naphthol[1,2-b]pyran as antiproliferatives:

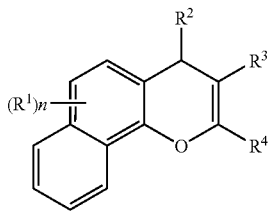

wherein,
- each $R^1$ is independently halo, trifluoromethyl, $C_{1-4}$ alkoxy, hydroxy, nitro, $C_{1-4}$ alkyl, $C_{1-4}$ alkylthio, hydroxy-$C_{1-4}$ alkyl, hydroxy-$C_{1-4}$ alkoxy, trifluoro-methoxy, carboxy, —COOR$^5$ where $R^5$ is an ester group, —CONR$^6$R$^7$ or —NR$^6$R$^7$ where $R^6$ and $R^7$ are each hydrogen or $C_{1-4}$ alkyl;
- $R^2$ is phenyl, naphthyl or heteroaryl selected from thienyl, pyridyl, benzothienyl quinolinyl, benzofuranyl or benzimidazolyl, wherein said phenyl, naphthyl and heteroaryl groups are optionally substituted, or $R^2$ is furanyl optionally substituted with $C_{1-4}$ alkyl;
- $R^3$ is nitrile, carboxy, —COOR$^8$ where $R^8$ is an ester group, —CONR$^9$R$^{10}$ where $R^9$ and $R^{10}$ are each hydrogen or $C_{1-4}$ alkyl or $R^{11}SO_2$ where $R^{11}$ is $C_{1-4}$ alkyl or optionally substituted phenyl;
- $R^4$ is —NR$^{12}$R$^{13}$, —NHCOR$^{12}$, —N(COR$^{12}$)$_2$ or —N=CHOCH$_2$R$^{12}$ where $R^{12}$ and $R^{13}$ are each hydrogen or $C_{1-4}$ alkyl optionally substituted with carboxy, or $R^4$ is

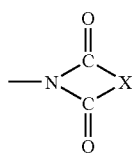

where X is $C_{2-4}$ alkylene, or $R^4$ is —NHSO$_2$R$^{14}$ where $R^{14}$ is $C_{1-4}$ alkyl or optionally substituted phenyl; and n is 0-2.

U.S. Pat. No. 5,281,619 discloses naphthopyrans for therapy of diabetic complications:

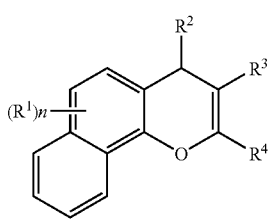

wherein,
- $R^1$ is $C_{1-4}$ alkoxy, OH or COOH;
- $R^2$ is optionally substituted phenyl;
- $R^3$ is nitrile, or $R^3$ is carboxy or —COOR$^8$ when $R^2$ is phenyl substituted with 3-nitro or 3-trifluoromethyl and $R^8$ is an ester group;
- $R^4$ is NR$^{12}$R$^{13}$, —NHCOR$^{12}$, —N(COR$^{12}$)$_2$ or —N=CHOCH$_2$R$^{12}$, wherein $R^{12}$ and $R^{13}$ are each H or $C_{1-4}$ alkyl; and n is 0-2.

EP599514 discloses the preparation of pyranoquinoline derivatives as inhibitors of cell proliferation:

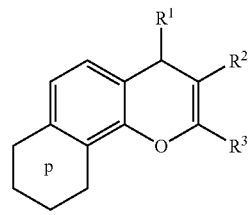

wherein $R^1$ is optionally substituted phenyl or optionally substituted heteroaryl selected from thienyl, pyridyl, benzothienyl, quinolinyl, benzofuranyl or benzimidazolyl, or $R^1$ is furanyl optionally substituted with $C_{1-4}$ alkyl;

$R^2$ is nitrile, carboxy, —CO$_2$R$^4$ wherein $R^4$ is an ester group, —CON(R$^5$)R$^6$ where $R^5$ and $R^6$ are independently H or $C_{1-4}$ alkyl, or $R^7SO_2$ where $R^7$ is $C_{1-4}$ alkyl or optionally substituted phenyl;

$R^3$ is —NR$^8$R$^9$, —NHCOR$^8$, —N(CO$_2$R$^8$)$_2$, —N=CHOR$^8$ where $R^8$ and $R^9$ are independently H or $C_{1-4}$ alkyl, or —NHSO$_2$R$^{10}$ where $R^{10}$ is $C_{1-4}$ alkyl or optionally substituted phenyl, or

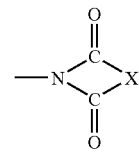

where X is $C_{2-4}$ alkylene; and the ring P represents a pyridine fused to the benzopyran nucleus.

EP618206 discloses the preparation of naphthopyran and pyranoquinoline as immunosuppressants and cell proliferation inhibitors:

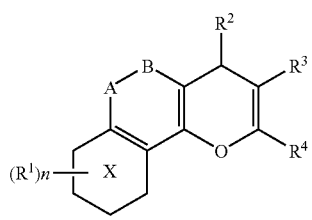

wherein,
- A-B is CH$_2$CH$_2$ or CH=CH;
- each $R^1$ is independently halo, carboxy, trifluoromethyl, hydroxy, $C_{1-4}$ alkyl, $C_{1-4}$ alkoxy, $C_{1-4}$ alkylthio, hydroxy-$C_{1-4}$alkyl, hydroxy-$C_{1-4}$ alkoxy, nitrogen-containing heterocyclyl, nitro, trifluoromethoxy, —COOR$^5$ where $R^5$ is an ester group, —COR$^6$, —CONR$^6$R$^7$ or —NR$^6$R$^7$ where $R^6$ and $R^7$ are each hydrogen or $C_{1-4}$ alkyl;
- $R^2$ is phenyl, naphthyl or heteroaryl selected from thienyl, pyridyl, benzothienyl, quinolinyl, benzofuranyl or benzimidazolyl, wherein said phenyl, naphthyl and heteroaryl groups are optionally substituted, or $R^2$ is furanyl optionally substituted with $C_{1-4}$ alkyl;

$R^3$ is nitrile, carboxy, —COOR$^8$ where R$^8$ is an ester group, —CONR$^9$R$^{10}$ where R$^9$ and R$^{10}$ are each hydrogen or C$_{1-4}$ alkyl, or —SO$_2$R$^{11}$ where R$^{11}$ is C$_{1-4}$ alkyl or optionally substituted phenyl-C$_{1-4}$ alkyl;

R$^4$ is 1-pyrrolyl, 1-imidazolyl or 1-pyrazolyl, each of which is optionally substituted by one or two C$_{1-4}$ alkyl, carboxyl, hydroxyl-C$_{1-4}$alkyl or —CHO groups, or R$^4$ is 1-(1,2,4-triazolyl), 1-(1,3,4-triazolyl) or 2-(1,2,3-triazolyl), each of which is optionally substituted by a C$_{1-4}$ alkyl or C$_{1-4}$ perfluoroalkyl group, or R$^4$ is 1-tetrazolyl optionally substituted by C$_{1-4}$ alkyl;

X is a pyridine or a benzene ring; and n is 0-2.

EP619314 discloses the preparation of 4-phenyl-4H-naphtho(2,1-b)pyran derivatives:

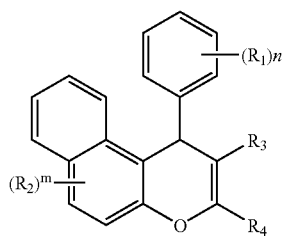

wherein,

R$_1$ and R$_2$ are independently halo, trifluoromethyl, C$_1$-C$_4$ alkoxy, hydroxy, nitro, C$_1$-C$_4$ alkyl, C$_1$-C$_4$ alkylthio, hydroxy-C$_1$-C$_4$ alkyl, hydroxy-C$_1$-C$_4$ alkoxy, trifluoromethoxy, carboxy, —COOR$_8$ where R$_8$ is an ester group, —COR$_9$, —CONR$_9$R$_{10}$ or —NR$_9$R$_{10}$ where R$_9$ and R$_{10}$ are each hydrogen or C$_1$-C$_4$ alkyl;

R$_3$ is nitrile, carboxy or —CO$_2$R$_{11}$ wherein R$_{11}$ is an ester group;

R$_4$ is —NR$_{12}$R$_{13}$, —NR$_{12}$COR$_{13}$, —N(COR$_{12}$)$_2$ or —N=CHOCH$_2$R$_{12}$ where R$_{12}$ and R$_{13}$ are each hydrogen or C$_{1-4}$ alkyl, or R$_4$ is

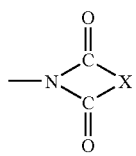

where X is C$_2$-C$_4$ alkylene, or R$_4$ is optionally substituted 1-pyrrolyl; and m and n are each independently 0-2.

The compounds are said to be useful for the treatment of restenosis, immune disease, and diabetic complications.

Smith, et al., (*Bioorg. Med. Chem. Lett.* 5:2783-2788 (1995)) reported the anti-rheumatic potential of a series of 2,4-di-substituted-4H-naphtho[1,2-b]pyran-3-carbonitriles. They reported that 4-(3-nitrophenyl)-2-(N-succinimido)-4H-naphtho[1,2-b]pyran-3-carbonitrile has proved to be acid stable and still retains biological activity:

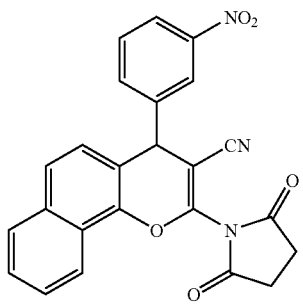

Birch, et al., (*Diabetes* 45:642-650 (1996)) reported that LY290181, an inhibitor of diabetes-induced vascular dysfunction, blocks protein kinase C-stimulated transcriptional activation through inhibition of transcription factor binding to a phorbol response element:

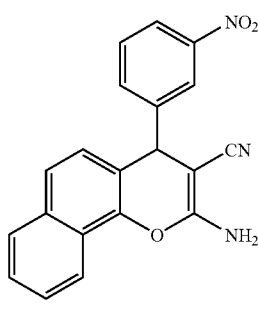

LY290181

Panda, et al., (*J. Biol. Chem.* 272: 7681-7687 (1997)) reported the suppression of microtubule dynamics by LY290181, which might be the potential mechanism for its antiproliferative action.

Wood, et al., (*Mol. Pharmacol.* 52: 437-444 (1997)) reported that LY290181 inhibited mitosis and microtubule function through direct tubulin binding.

PCT published patent application WO9824427 disclosed antimicrotubule compositions and methods for treating or preventing inflammatory diseases. LY290181 was listed as an antimicrotubule agent.

PCT published patent application WO0134591 disclosed 4H-chromenes and analogs as activators of caspases and inducers of apoptosis:

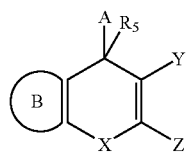

wherein,

X is O, S or NR$_6$, wherein R$_6$ is hydrogen or optionally substituted alkyl;

Y is CN, COR$_7$, CO$_2$R$_7$ or CONR$_x$R$_y$, wherein R$_7$, R$_x$ and R$_y$ are independently hydrogen, C$_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together with the nitrogen to which they are attached to form a heterocycle;

Z is $NR_8R_9$, $NHCOR_8$, $N(COR_8)_2$, $N(COR_8)(COR_9)$, $N=CHOR_8$ or $N=CHR_8$, wherein $R_8$ and $R_9$ are independently H, $C_{1-4}$ alkyl or aryl, or $R_8$ and $R_9$ are combined together with the group attached to them to form a heterocycle;

$R_5$ is hydrogen or $C_{1-10}$ alkyl;

A is optionally substituted and is aryl, heteroaryl, saturated carbocyclic, partially saturated carbocyclic, saturated heterocyclic, partially saturated heterocyclic, arylalkyl or heteroarylalkyl; and B is an optionally substituted aromatic or heteroaromatic ring.

PCT published patent application WO02092076 disclosed substituted coumarins and quinolines and analogs as activators of caspases and inducers of apoptosis:

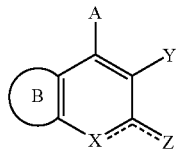

wherein, the dashed lines cannot both be a double bond at the same time;

X is O, S or $NR_6$, wherein $R_6$ is hydrogen or optionally substituted alkyl or aryl;

Y is CN, $COR_7$, $CO_2R_7$ or $CONR_xR_y$, wherein $R_7$, $R_x$ and $R_y$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together with the nitrogen to which they are attached to form a heterocycle;

Z is O, S, halo, $NR_8$, or $NCOR_8$, wherein $R_8$ is independently H, $C_{1-4}$ alkyl or aryl;

A is optionally substituted and is aryl, heteroaryl, saturated carbocyclic, partially saturated carbocyclic, saturated heterocyclic, partially saturated heterocyclic, arylalkyl or heteroarylalkyl; and B is optionally substituted and is an aryl, heteroaryl, saturated carbocyclic, partially saturated carbocyclic, saturated heterocyclic, or partially saturated heterocyclic ring.

PCT published patent application WO02092083 disclosed 7,8-fused 4H-chromene and analogs as activators of caspases and inducers of apoptosis:

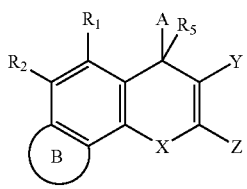

wherein,

X is O, S or $NR_6$, wherein $R_6$ is hydrogen or optionally substituted alkyl;

Y is CN, $COR_7$, $CO_2R_7$ or $CONR_xR_y$, wherein $R_7$, $R_x$ and $R_y$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together with the nitrogen to which they are attached to form a heterocycle;

Z is $NR_8R_9$, $NHCOR_8$, $N(COR_8)_2$, $N(COR_8)(COR_9)$, $N=CHOR_8$ or $N=CHR_8$, wherein $R_8$ and $R_9$ are independently H, $C_{1-4}$ alkyl or aryl, or $R_8$ and $R_9$ are combined together with the group attached to them to form a heterocycle;

$R_1$-$R_2$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl aminoalkyl, carboxyalkyl, nitro, amino, cyano, acylamido, hydroxy, thiol, acyloxy, azido, alkoxy, carboxy, methylenedioxy, carbonylamido or alkylthiol;

$R_5$ is hydrogen or $C_{1-10}$ alkyl;

A is optionally substituted and is aryl, heteroaryl, saturated carbocyclic, partially saturated carbocyclic, saturated heterocyclic, partially saturated heterocyclic, arylalkyl or heteroarylalkyl; and B is optionally substituted and is a fused thiazole, oxazole, 2-imino-imidazole, 2,1,3-thiadiazo-2-one, thiazol-2-one, oxazol-2-one, imidazol-2-thione, thiazol-2-thione, oxazol-2-thione, imidazoline, oxazoline, thiazoline, triazole, oxazine, oxazine-2,3-dione, or piperazine ring.

PCT published patent application WO02092594 disclosed substituted 4H-chromenes and analogs as activators of caspases and inducers of apoptosis:

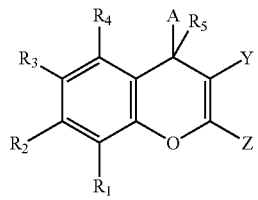

wherein, $R_1$-$R_4$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or $R_1$ and $R_2$, or $R_2$ and $R_3$, or $R_3$ and $R_4$, taken together with the atoms to which they are attached form an aryl, heteroaryl, partially saturated carbocyclic or partially saturated heterocyclic group, wherein said group is optionally substituted;

$R_5$ is hydrogen or $C_{1-10}$ alkyl;

A is optionally substituted and is aryl, heteroaryl, saturated carbocyclic, partially saturated carbocyclic, saturated heterocyclic, partially saturated heterocyclic or arylalkyl;

Y is CN, $COR_7$, $CO_2R_7$ or $CONR_xR_y$, wherein $R_7$, $R_x$ and $R_y$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together with the nitrogen to which they are attached to form a heterocycle; and Z is $NR_8R_9$, $NHCOR_8$, $N(COR_9)_2$, $N(COR_8)(COR_9)$, $N=CHOR_8$ or $N=CHR_8$, wherein $R_8$ and $R_9$ are independently H, $C_{1-4}$ alkyl or aryl, or $R_8$ and $R_9$ are combined together with the group attached to them to form a heterocycle.

SUMMARY OF THE INVENTION

The present invention is related to the discovery that substituted 4H-chromene and analogs, as represented in Formula I, are activators of the caspase cascade and inducers of apoptosis. Thus, an aspect of the present invention is directed to the use of compounds of Formula I as inducers of apoptosis.

A second aspect of the present invention is to provide a method for treating, preventing or ameliorating neoplasia and cancer by administering a compound of Formula I to a mammal in need of such treatment.

Many of the compounds within the scope of the present invention are novel compounds. Therefore, a third aspect of the present invention is to provide novel compounds of Formula I, and to also provide for the use of these novel compounds for treating, preventing or ameliorating neoplasia and cancer.

A fourth aspect of the present invention is to provide a pharmaceutical composition useful for treating disorders responsive to the induction of apoptosis, containing an effective amount of a compound of Formula I in admixture with one or more pharmaceutically acceptable carriers or diluents.

A fifth aspect of the present invention is directed to methods for the preparation of novel compounds of Formula I.

DETAILED DESCRIPTION OF THE INVENTION

The present invention arises out of the discovery that substituted 4H-chromene and analogs, as represented in Formula I, are potent and highly efficacious activators of the caspase cascade and inducers of apoptosis. Therefore, compounds of Formula I are useful for treating disorders responsive to induction of apoptosis.

Specifically, compounds useful in this aspect of the present invention are represented by Formula I:

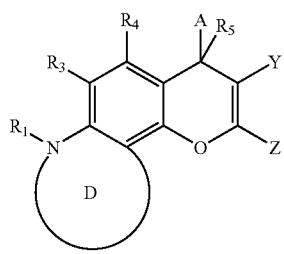

(I)

wherein, $R_1$ is selected from the group consisting of alkyl, cycloalkyl, cycloalkylalkyl, hydroxyalkyl, haloalkyl, alkoxyalkyl, aminoalkyl and oxiranylalkyl;

$R_3$ and $R_4$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol;

$R_5$ is hydrogen or $C_{1-10}$ alkyl;

A is optionally substituted and is aryl, heteroaryl, saturated carbocyclic, partially saturated carbocyclic, saturated heterocyclic, partially saturated heterocyclic or arylalkyl;

D is optionally substituted and is a heteroaromatic, partially saturated heterocyclic or saturated heterocyclic fused ring, wherein said fused ring has 5 or 6 ring atoms, wherein one or two of said ring atoms are nitrogen atoms and the others of said ring atoms are carbon atoms;

Y is CN, $COR_{19}$, $CO_2R_{19}$ or $CONR_{20}R_{21}$, wherein $R^{19}$, $R_{20}$ and $R_{21}$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_{20}$ and $R_{21}$ are taken together with the nitrogen to form a heterocycle; and Z is $NR_{22}R_{23}$, $NHCOR_{22}N(COR_{23})_2$, $N(COR_{22})(COR_{23})$, $N=CHOR_{19}$ or $N=CHR_{19}$ wherein $R_{22}$ and $R_{23}$ are independently H, $C_{1-4}$ alkyl or aryl, or $R_{22}$ and $R_{23}$ are combined together with the group attached to them to form a heterocycle;

or a pharmaceutically acceptable salt or prodrug thereof.

Preferably $R^1$ is selected from the group consisting of alkyl, cycloalkylalkyl, hydroxyalkyl, haloalkyl, aminoalkyl and oxiranylalkyl. More preferably $R_1$ is methyl or hydroxymethyl; most preferably, methyl. Preferably each of $R_3$-$R_5$ is hydrogen, hydroxy, methoxy or alkyl; more preferably, hydrogen.

Preferably Y is cyano. Preferably Z is $NR_{22}R_{23}$ where $R_{22}$ and $R_{23}$ are independently H, $C_{1-4}$ alkyl or aryl; more preferably, H or $C_{1-4}$ alkyl. Most preferably Z is $NH_2$.

Preferably A is optionally substituted and selected from the group consisting of phenyl, pyridinyl, pyrazinyl, quinoxalinyl, indolyl and thiophenyl. More preferably, A is optionally substituted phenyl or optionally substituted pyridyl. Preferred substituents on the phenyl group include halo, hydroxy, methyl and methoxy. Preferred substituents on the pyridyl group include halo, methoxy and methyl. Particularly preferred are 3-methoxyphenyl, 3-bromophenyl, 3-bromo-4,5-dimethoxyphenyl, 5-methylpyridin-3-yl and 5-bromo-pyridin-3-yl.

When A is optionally substituted phenyl, A may be:

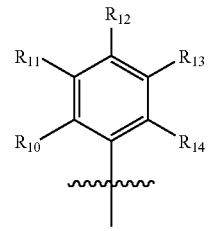

wherein: $R_{10}$-$R_{14}$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, ethylenedioxy, carbonylamido or alkylthiol; or $R_{10}$ and $R_{11}$, or $R_{11}$ and $R_{12}$, taken together with the atoms to which they are attached form an aryl, heteroaryl, optionally substituted carbocyclic or optionally substituted heterocyclic group, wherein said group is optionally substituted.

When A is optionally substituted pyridyl, A may be:

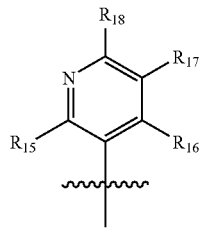

and $R_{15}$-$R_{18}$ are independently hydrogen, halo, haloalkyl, aryl, fused aryl, carbocyclic, aheterocyclic group, a heteroaryl group, $C_{1-10}$ alkyl, alkenyl, alkynyl, arylalkyl, arylalkenyl, arylalkynyl, heteroarylalkyl, heteroarylalkenyl, heterocycloalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, ethylenedioxy, carbonylamido or alkyithiol; or $R_{16}$ and $R_{17}$, or $R_{17}$ and $R_{18}$, taken together with the atoms to which they are attached form an aryl, heteroaryl, optionally substituted carbocyclic or optionally substituted heterocyclic group, wherein said group is optionally substituted.

Preferably D is selected from the group consisting of:

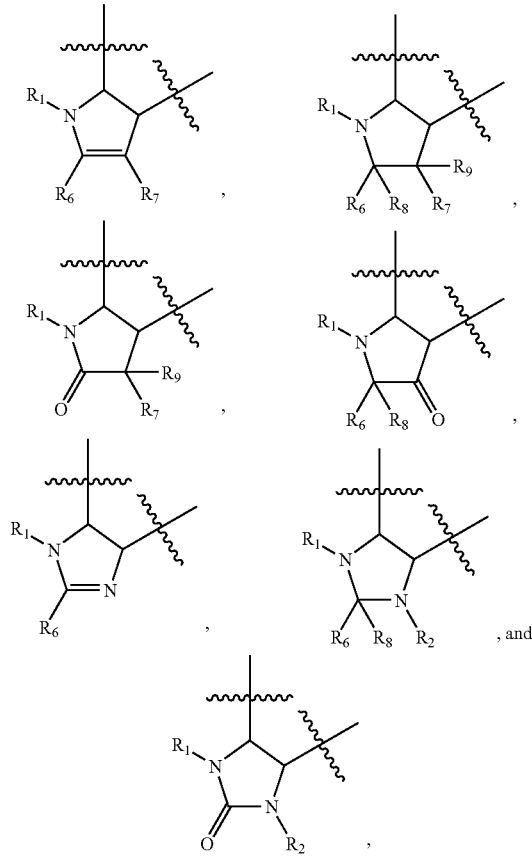

wherein, $R_2$ is selected from the group consisting of is hydrogen, $C_{1-10}$ alkyl, haloalkyl, aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl;

and each of $R_6$-$R_9$ is independently selected from the group consisting of hydrogen, halo, haloalkyl, aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido and alkylthiol.

If present, $R_2$ is preferably hydrogen or alkyl; more preferably hydrogen or methyl. If present, $R_2$ is most preferably hydrogen.

If present, each of $R_6$-$R_9$ is preferably hydrogen, halogen, hydroxy, alkyl or alkoxy. If present, each of $R_6$-$R_9$ is preferably hydrogen or alkyl. Most preferably each of $R_6$-$R_9$ is hydrogen.

One embodiment of the present invention is directed to compounds of Formula II:

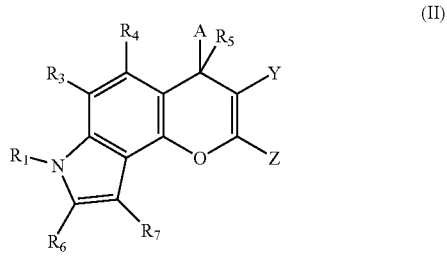

(II)

and pharmaceutically acceptable salts and prodrugs thereof, where $R_1$, $R_3$-$R_7$, A, Y and Z are as defined above.

Another embodiment of the present invention is directed to compounds Formula III:

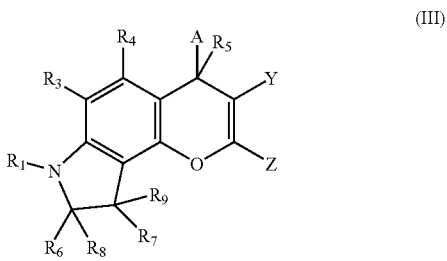

(III)

and pharmaceutically acceptable salts and prodrugs thereof, wherein $R_1$, $R_3$-$R_9$, A, Y and Z are as defined above.

Another embodiment of the present invention is directed to compounds of Formula IV:

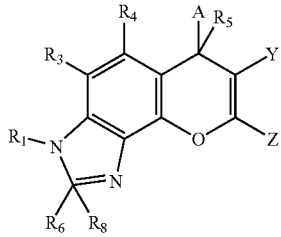

(IV)

and pharmaceutically acceptable salts and prodrugs thereof, wherein $R_1$, $R_3$-$R_6$, A, Y and Z are as defined above.

Exemplary preferred compounds that may be employed in the method of the invention include, without limitation:

2-Amino-4-(5-cyano-pyridin-3-yl)-3-cyano-7-methyl-4H-pyrrolo[2,3-h]chromene;
2-Amino-3-cyano-7-methyl-4-(6-methyl-pyrazin-2-yl)-4H-pyrrolo[2,3-h]chromene;
2-Amino-3-cyano-7-methyl-4-(quinoxalin-2-yl)-4H-pyrrolo[2,3-h]chromene;
2-Amino-4-(3-bromo-4,5-dimethoxyphenyl)-3-cyano-7-ethyl-4H-pyrrolo[2,3-h]chromene;
2-Amino-4-(3-bromo-4,5-dimethoxyphenyl)-3-cyano-7-cyclopropylmethyl-4H-pyrrolo[2,3-h]chromene;
2-Amino-4-(3-bromo-4,5-dimethoxyphenyl)-3-cyano-7-(2-diethylamino-ethyl)-4H-pyrrolo[2,3-h]chromene;
2-Amino-4-(5-chloro-pyridin-3-yl)-3-cyano-7-methyl-4H-pyrrolo[2,3-h]chromene;
2-Amino-3-cyano-4-(indol-3-yl)-7-methyl-4H-pyrrolo[2,3-h]chromene;
2-Amino-4-(5-chloro-6-hydroxy-pyridin-3-yl)-3-cyano-7-methyl-4H-pyrrolo[2,3-h]chromene;
2-Amino-3-cyano-4-(5-methyl-pyridin-3-yl)-7-methyl-4H-pyrrolo[2,3-h]chromene;
2-Amino-4-(5-bromo-pyridin-3-yl)-3-cyano-7-methyl-4H-pyrrolo[2,3-h]chromene;
2-Amino-4-(3-bromo-4,5-dimethoxyphenyl)-3-cyano-7-methyl-4H-imidazo[4,5-h]chromene;
2-Amino-4-(5-bromo-pyridin-3-yl)-3-cyano-7-methyl-4H-imidazo[4,5-h]chromene;
2-Amino-3-cyano-4-(5-methyl-pyridin-3-yl)-7-methyl-4H-imidazo[4,5-h]chromene;
2-Amino-4-(3-bromo-4,5-dimethoxyphenyl)-3-cyano-7-methyl-4H-pyrrolo [2,3-h]chromene;
2-Amino-4-(3-bromo-4,5-dimethoxyphenyl)-3-cyano-7-hydroxymethyl-4H-pyrrolo[2,3-h]chromene;
2-Amino-4-(3-bromo-4-hydroxy-5-methoxyphenyl)-3-cyano-7-methyl-4H-pyrrolo[2,3-h]chromene;
2-Amino-4-(3-bromo-4,5-dimethoxyphenyl)-3-cyano-7-oxiranylmethyl-4H-pyrrolo[2,3-h]chromene;
2-Amino-3-cyano-4-(5-methyl-pyridin-3-yl)-7-hydroxymethyl-4H-pyrrolo[2,3-h]chromene;
2-Amino-4-(5-bromo-pyridin-3-yl)-3-cyano-7-hydroxymethyl-4H-pyrrolo[2,3-h]chromene;
2-Amino-4-(4-acetoxy-3-bromo-5-methoxyphenyl)-3-cyano-7-methyl-4H-pyrrolo[2,3-h]chromene;
2-Amino-4-(3-bromo-4,5-dimethoxyphenyl)-3-cyano-8,9-dihydro-7-methyl-4H-pyrrolo[2,3-h]chromene;
2-Amino-3-cyano-4-(3,4,5-trimethoxyphenyl)-7-methyl-4H-pyrrolo[2,3-h]chromene;
2-Amino-3-cyano-4-(3-nitrophenyl)-7-methyl-4H-pyrrolo[2,3-h]chromene;
2-Amino-3-cyano-4-(3,5-dimethoxyphenyl)-7-methyl-4H-pyrrolo[2,3-h]chromene;
2-Amino-3-cyano-4-(3,4-methylenedioxo-5-methoxyphenyl)-7-methyl-4H-pyrrolo[2,3-h]chromene;
2-Amino-3-cyano-4-(3-methoxyphenyl)-7-methyl-4H-pyrrolo[2,3-h]chromene;
2-Amino-3-cyano-4-(3-bromophenyl)-7-methyl-4H-pyrrolo[2,3-h]chromene;
2-Amino-3-cyano-4-(3,5-difluorophenyl)-7-methyl-4H-pyrrolo[2,3-h]chromene;
2-Amino-3-cyano-4-(4,5-dimethoxy-3-iodophenyl)-7-methyl-4H-pyrrolo[2,3-h]chromene;
2-Amino-3-cyano-4-(3-cyanophenyl)-7-methyl-4H-pyrrolo[2,3-h]chromene;
2-Amino-3-cyano-4-(3,4,5-trimethoxyphenyl)-7-hydroxymethyl-4H-pyrrolo[2,3-h]chromene;
2-Amino-3-cyano-4-(3,5-dimethoxyphenyl)-7-hydroxymethyl-4H-pyrrolo[2,3-h]chromene;
2-Amino-3-cyano-4-(3,5-difluorophenyl)-8,9-dihydro-7-methyl-4H-pyrrolo[2,3-h]chromene;
2-Amino-4-(5-methyl-pyridin-3-yl)-3-cyano-7-methyl-8,9-dihydro-4H-pyrrolo[2,3-h]chromene;
2-Amino-4-(5-nitro-thiophene-2-yl)-3-cyano-7-methyl-4H-pyrrolo[2,3-h]chromene;
4,7,10,13,16,19-Docosahexaenoic acid {2-Amino-4-(3-bromo-4,5-dimethoxyphenyl)-3-cyano-4H-pyrrolo[2,3-h]chromene}-7-ylmethyl ester;
4,7,10,13,16,19-Docosahexaenoic acid {2-Amino-3-cyano-4-(5-methyl-pyridin-3-yl)-4H-pyrrolo[2,3-h]chromene}-7-ylmethyl ester;
2-Amino-3-cyano-4-(3-fluorophenyl)-7-methyl-4H-pyrrolo[2,3-h]chromene;
2-Amino-3-cyano-4-(4-cyanophenyl)-7-methyl-4H-pyrrolo[2,3-h]chromene;
2-Amino-3-cyano-4-(3-chlorophenyl)-7-methyl-4H-pyrrolo[2,3-h]chromene;
2-Amino-3-cyano-4-(3,5-dichlorophenyl)-7-methyl-4H-pyrrolo[2,3-h]chromene;
2-Amino-3-cyano-4-(3,4-dichlorophenyl)-7-methyl-4H-pyrrolo[2,3-h]chromene;
2-Amino-3-cyano(3-bromo-4,5-dimethoxyphenyl)-7,9-dimethyl-4H-pyrrolo[2,3-h]chromene;
2-Amino-3-cyano-4-(3,4-difluorophenyl)-7-methyl-4H-pyrrolo[2,3-h]chromene;
2-Amino-3-cyano-4-(3-fluoro-4-chlorophenyl)-7-methyl-4H-pyrrolo[2,3-h]chromene;
2-Amino-3-cyano-4-(3-bromo-4-fluorophenyl)-7-methyl-4H-pyrrolo[2,3-h]chromene;
2-Amino-3-cyano-4-(3-cyano-4-fluorophenyl)-7-methyl-4H-pyrrolo[2,3-h]chromene;
2-Amino-3-cyano-4-(5-methoxy-pyridin-3-yl)-7-methyl-4H-pyrrolo[2,3-h]chromene;
2-Amino-3-cyano-4-(3,5-dichloro-phenyl)-7-isopropyl-4H-pyrrolo[2,3-h]chromene;
2-Amino-3-cyano-4-(3-bromo-4,5-dimethoxy-phenyl)-7-isopropyl-4H-pyrrolo[2,3-h]chromene;

and pharmaceutically acceptable salts or prodrugs thereof.

The present invention is also directed to novel compounds within the scope of Formulae I-III:

2-Amino-4-(5-cyano-pyridin-3-yl)-3-cyano-7-methyl-4H-pyrrolo[2,3-h]chromene;
2-Amino-3-cyano-7-methyl-4-(6-methyl-pyrazin-2-yl)-4H-pyrrolo[2,3-h]chromene;
2-Amino-3-cyano-7-methyl-4-(quinoxalin-2-yl)$_4$H-pyrrolo[2,3-h]chromene;
2-Amino-4-(3-bromo-4,5-dimethoxyphenyl)-3-cyano-7-ethyl-4H-pyrrolo[2,3-h]chromene;
2-Amino-4-(3-bromo-4,5-dimethoxyphenyl)-3-cyano-7-cyclopropylmethyl-4H-pyrrolo[2,3-h]chromene;
2-Amino-4-(3-bromo-4,5-dimethoxyphenyl)-3-cyano-7-(2-diethylamino-ethyl)$_4$H-pyrrolo[2,3-h]chromene;

2-Amino-4-(5-chloro-pyridin-3-yl)-3-cyano-7-methyl-4H-pyrrolo[2,3-h]chromene;

2-Amino-3-cyano-4-(indol-3-yl)-7-methyl-4H-pyrrolo[2,3-h]chromene;

2-Amino-4-(5-chloro-6-hydroxy-pyridin-3-yl)-3-cyano-7-methyl-4H-pyrrolo[2,3-h]chromene;

2-Amino-3-cyano-4-(5-methyl-pyridin-3-yl)-7-methyl-4H-pyrrolo[2,3-h]chromene;

2-Amino-4-(5-bromo-pyridin-3-yl)-3-cyano-7-methyl-4H-pyrrolo[2,3-h]chromene;

2-Amino-4-(3-bromo-4,5-dimethoxyphenyl)-3-cyano-7-methyl-4H-imidazo[4,5-h]chromene;

2-Amino-4-(5-bromo-pyridin-3-yl)-3-cyano-7-methyl-4H-imidazo[4,5-h]chromene;

2-Amino-3-cyano-4-(5-methyl-pyridin-3-yl)-7-methyl-4H-imidazo[4,5-h]chromene;

2-Amino-4-(3-bromo-4,5-dimethoxyphenyl)-3-cyano-7-methyl-4H-pyrrolo[2,3-h]chromene;

2-Amino-4-(3-bromo-4,5-dimethoxyphenyl)-3-cyano-7-hydroxy-methyl-4H-pyrrolo[2,3-h]chromene;

2-Amino-4-(3-bromo-4-hydroxy-5-methoxyphenyl)-3-cyano-7-methyl-4H-pyrrolo[2,3-h]chromene;

2-Amino-4-(3-bromo-4,5-dimethoxyphenyl)-3-cyano-7-oxiranylmethyl-4H-pyrrolo[2,3-h]chromene;

2-Amino-3-cyano-4-(5-methyl-pyridin-3-yl)-7-hydroxymethyl-4H-pyrrolo[2,3-h]chromene;

2-Amino-4-(5-bromo-pyridin-3-yl)-3-cyano-7-hydroxymethyl-4H-pyrrolo[2,3-h]chromene;

2-Amino-4-(4-acetoxy-3-bromo-5-methoxyphenyl)-3-cyano-7-methyl-4H-pyrrolo[2,3-h]chromene;

2-Amino-4-(3-bromo-4,5-dimethoxyphenyl)-3-cyano-8,9-dihydro-7-methyl-4H-pyrrolo[2,3-h]chromene;

2-Amino-3-cyano-4-(3,4,5-trimethoxyphenyl)-7-methyl-4H-pyrrolo[2,3-h]chromene;

2-Amino-3-cyano-4-(3-nitrophenyl)-7-methyl-4H-pyrrolo[2,3-h]chromene;

2-Amino-3-cyano-4-(3,5-dimethoxyphenyl)-7-methyl-4H-pyrrolo[2,3-h]chromene;

2-Amino-3-cyano-4-(3,4-methylenedioxo-5-methoxyphenyl)-7-methyl-4H-pyrrolo[2,3-h]chromene;

2-Amino-3-cyano-4-(3-methoxyphenyl)-7-methyl-4H-pyrrolo[2,3-h]chromene;

2-Amino-3-cyano-4-(3-bromophenyl)-7-methyl-4H-pyrrolo[2,3-h]chromene;

2-Amino-3-cyano-4-(3,5-difluorophenyl)-7-methyl-4H-pyrrolo[2,3-h]chromene;

2-Amino-3-cyano-4-(4,5-dimethoxy-3-iodophenyl)-7-methyl-4H-pyrrolo[2,3-h]chromene;

2-Amino-3-cyano-4-(3-cyanophenyl)-7-methyl-4H-pyrrolo[2,3-h]chromene;

2-Amino-3-cyano-4-(3,4,5-trimethoxyphenyl)-7-hydroxymethyl-4H-pyrrolo[2,3-h]chromene;

2-Amino-3-cyano-4-(3,5-dimethoxyphenyl)-7-hydroxymethyl-4H-pyrrolo[2,3-h]chromene;

2-Amino-3-cyano-4-(3,5-difluorophenyl)-8,9-dihydro-7-methyl-4H-pyrrolo[2,3-h]chromene;

2-Amino-4-(5-methyl-pyridin-3-yl)-3-cyano-7-methyl-8,9-dihydro-4H-pyrrolo[2,3-h]chromene;

2-Amino-(5-nitro-thiophene-2-yl)-3-cyano-7-methyl-4H-pyrrolo[2,3-h]chromene;

4,7,10,13,16,19-Docosahexaenoic acid {2-Amino-4-(3-bromo-4,5-dimethoxyphenyl)-3-cyano-4H-pyrrolo[2,3-h]chromene}-7-ylmethyl ester;

4,7,10,13,16,19-Docosahexaenoic acid {2-Amino-3-cyano-4-(5-methyl-pyridin-3-yl)-4H-pyrrolo[2,3-h]chromene}-7-ylmethyl ester;

2-Amino-3-cyano-4-(3-fluorophenyl)-7-methyl-4H-pyrrolo[2,3-h]chromene 2-Amino-3-cyano-4-(4-cyanophenyl)-7-methyl-4H-pyrrolo[2,3-h]chromene;

2-Amino-3-cyano-4-(3-chlorophenyl)-7-methyl-4H-pyrrolo[2,3-h]chromene;

2-Amino-3-cyano-4-(3,5-dichlorophenyl)-7-methyl-4H-pyrrolo[2,3-h]chromene;

2-Amino-3-cyano-4-(3,4-dichlorophenyl)-7-methyl-4H-pyrrolo[2,3-h]chromene;

2-Amino-3-cyano-4-(3-bromo-4,5-dimethoxyphenyl)-7,9-dimethyl-4H-pyrrolo[2,3-h]chromene;

2-Amino-3-cyano-4-(3,4-difluorophenyl)-7-methyl-4H-pyrrolo[2,3-h]chromene;

2-Amino-3-cyano-4-(3-fluoro-4-chlorophenyl)-7-methyl-4H-pyrrolo[2,3-h]chromene;

2-Amino-3-cyano-4-(3-bromo-4-fluorophenyl)-7-methyl-4H-pyrrolo[2,3-h]chromene;

2-Amino-3-cyano-4-(3-cyano-4-fluorophenyl)-7-methyl-4H-pyrrolo[2,3-h]chromene;

2-Amino-3-cyano-4-(5-methoxy-pyridin-3-yl)-7-methyl-4H-pyrrolo[2,3-h]chromene;

2-Amino-3-cyano-4-(3,5-dichloro-phenyl)-7-isopropyl-4H-pyrrolo[2,3-h]chromene;

2-Amino-3-cyano-4-(3-bromo-4,5-dimethoxy-phenyl)-7-isopropyl-4H-pyrrolo[2,3-h]chromene;

and pharmaceutically acceptable salts or prodrugs thereof.

Certain of the compounds of the present invention may exist as stereoisomers including optical isomers. The invention includes all stereoisomers and both the racemic mixtures of such stereoisomers, as well as the individual enantiomers that may be separated according to methods that are well known to those of ordinary skill in the art.

Examples of pharmaceutically acceptable addition salts include inorganic and organic acid addition salts, such as hydrochloride, hydrobromide, phosphate, sulphate, citrate, lactate, tartrate, maleate, fumarate, mandelate and oxalate; and inorganic and organic base addition salts with bases, such as sodium hydroxy, Tris(hydroxymethyl)aminomethane (TRIS, tromethane) and N-methyl-glucamine.

Examples of prodrugs of the compounds of the invention include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-40}$ carboxylic acid, such as 4,7,10,13,16,19-docosahexaenoic acid (DHA), $C_{3-6}$ dioic acid or anhydride thereof, such as succinic and fumaric anhydrides according to methods known in the art); imines of amino containing compounds (e.g., those obtained by condensation with a $C_{1-4}$ aldehyde or ketone according to methods known in the art); carbamate of amino containing compounds, such as those described by Leu, et. al., (*J. Med. Chem.* 42:3623-3628 (1999)) and Greenwald, et. al., (*J. Med. Chem.* 42:3657-3667 (1999)); acetals and ketals of alcohol containing compounds (e.g., those obtained by condensation with chloromethyl methyl ether or chloromethyl ethyl ether according to methods known in the art); and phosphonate and phosphono compounds (e.g., those obtained by condensation with a phosphate ester, phosphoryl chloride, or phosphoric acid), which include pharmaceutically acceptable mono-basic and di-basic addition salts of the phosphono group, e.g., organic bases, such as amine bases, which include ammonia, piperidine and morpholine.

Compounds of Formula I can be prepared as illustrated by exemplary reaction in Scheme 1. Reaction of 4-benzyloxy-indole with MeI in the presence of a base such as NaH produced 4-benzyloxy-1-methyl-indole. The benzyl protecting group was removed by hydrogenation to give the 4-hydroxy-1-methyl-indole. Reaction of 4-hydroxy-1-methyl-indole with an aryl-aldehyde such as 5-bromoveratraldehyde and malononitrile in the presence of a base such as piperidine produced the substituted 7-methyl-pyrrolo[2,3-h]chromene.

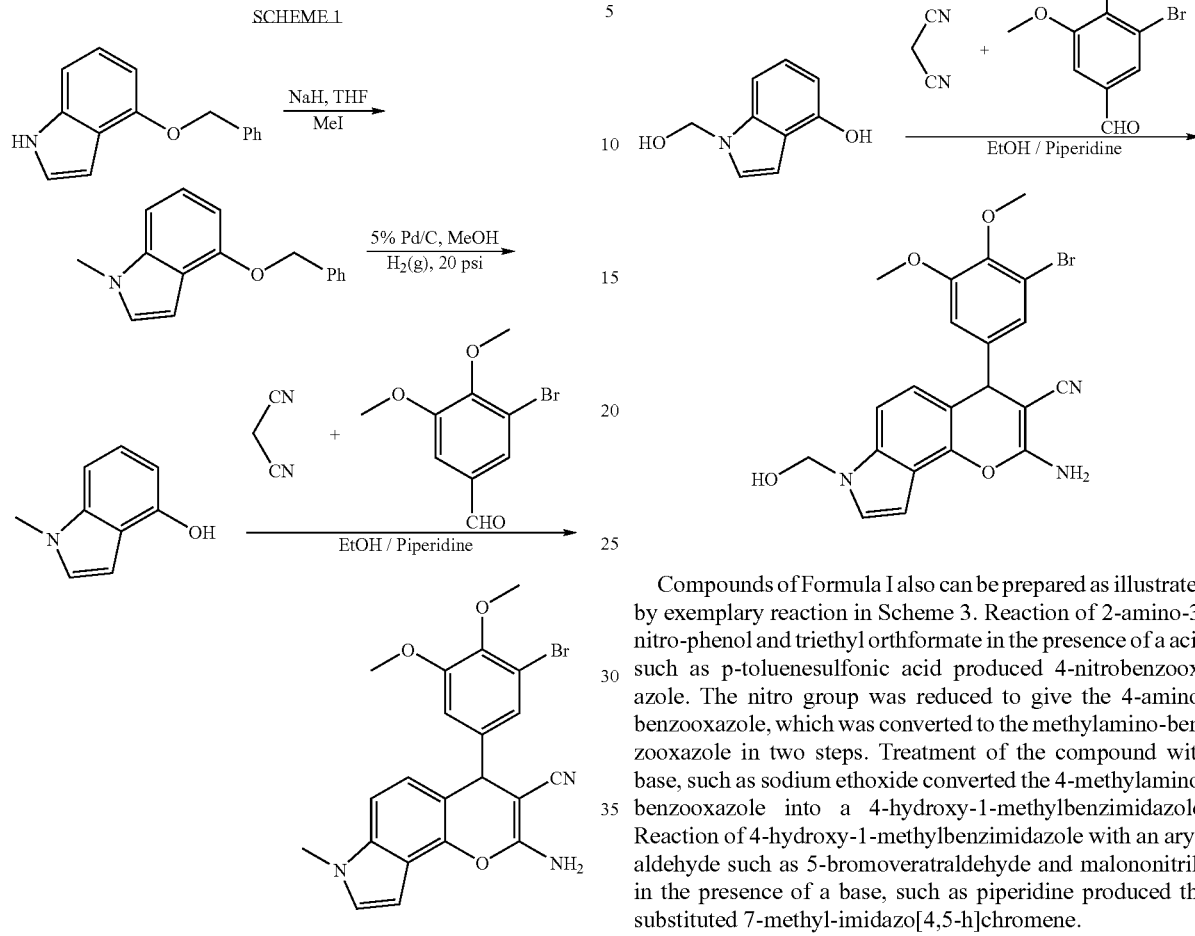

Compounds of Formula I also can be prepared as illustrated by exemplary reaction in Scheme 2. Reaction of 4-benzyloxy-indole with formaldehyde in the presence of a base such as NaOH produced 4-benzyloxy-1-hydroxymethyl-indole. The benzyl protecting group was removed by hydrogenation to give the 4-hydroxy-1-hydroxymethyl-indole. Reaction of 4-hydroxy-1-hydroxymethyl-indole with an aryl-aldehyde, such as 5-bromoveratraldehyde and malononitrile in the presence of a base, such as piperidine produced the substituted 7-hydroxymethyl-pyrrolo[2,3-h]chromene.

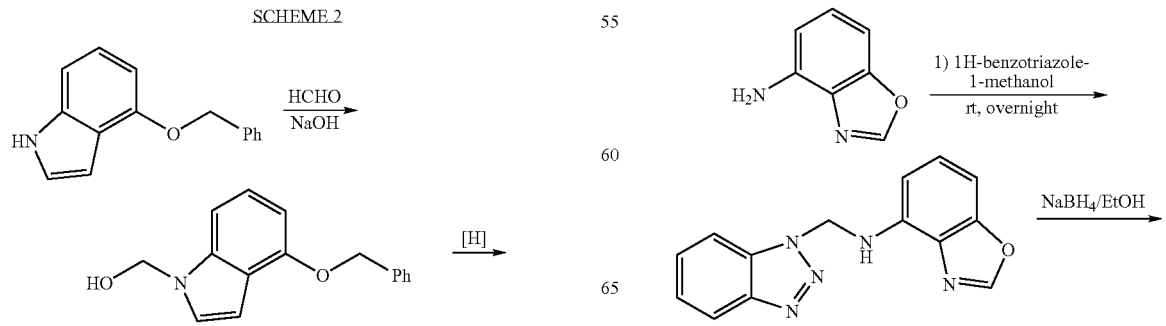

Compounds of Formula I also can be prepared as illustrated by exemplary reaction in Scheme 3. Reaction of 2-amino-3-nitro-phenol and triethyl orthformate in the presence of a acid such as p-toluenesulfonic acid produced 4-nitrobenzooxazole. The nitro group was reduced to give the 4-amino-benzooxazole, which was converted to the methylamino-benzooxazole in two steps. Treatment of the compound with base, such as sodium ethoxide converted the 4-methylamino-benzooxazole into a 4-hydroxy-1-methylbenzimidazole. Reaction of 4-hydroxy-1-methylbenzimidazole with an aryl-aldehyde such as 5-bromoveratraldehyde and malononitrile in the presence of a base, such as piperidine produced the substituted 7-methyl-imidazo[4,5-h]chromene.

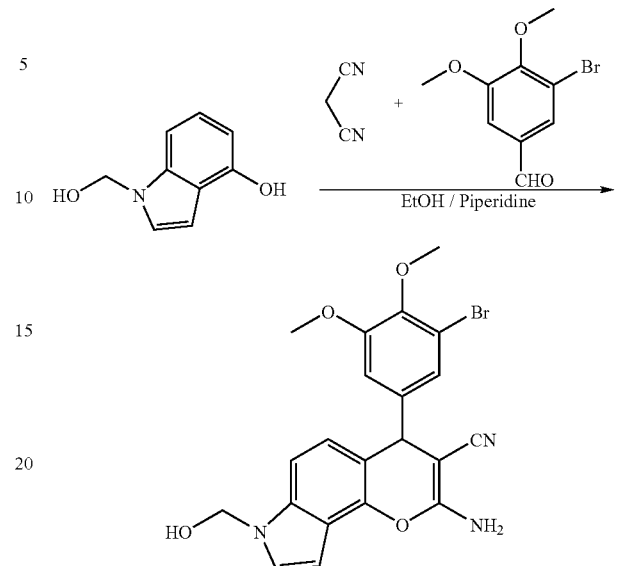

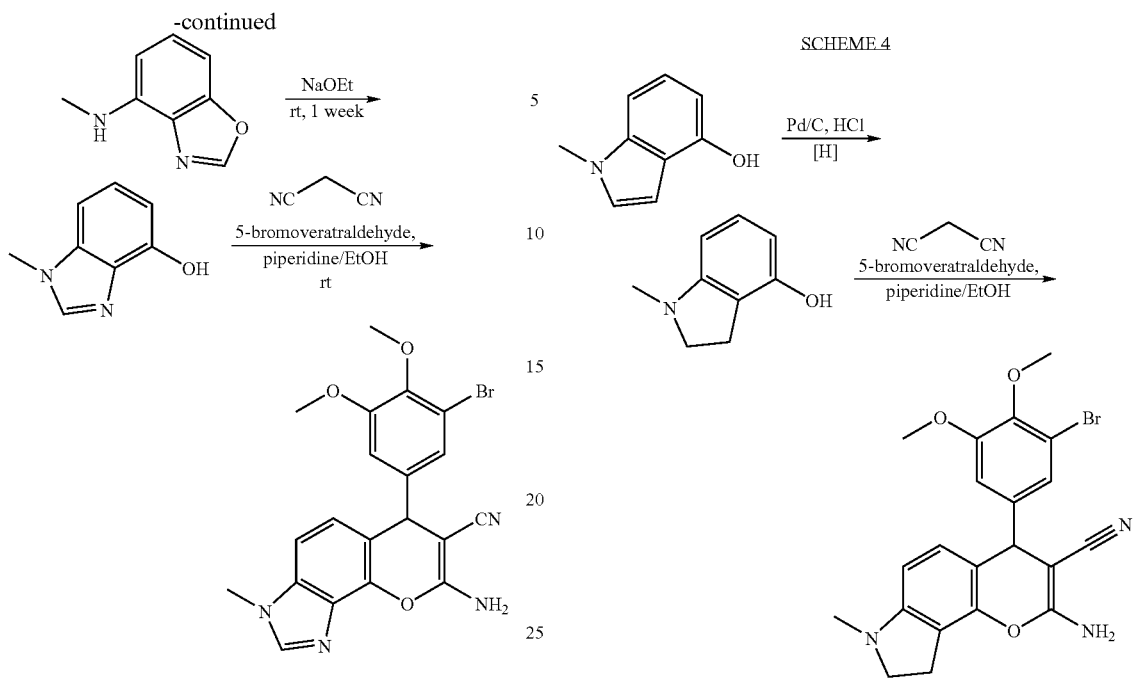

Compounds of Formula I also can be prepared as illustrated by exemplary reaction in Scheme 4. Reduction of 4-hydroxy-1-methyl-indole by hydrogenation in the presence of an acid such as HCl produced the 4-hydroxy-2,3-dihydro-1-methyl-indole. Reaction of 4-hydroxy-2,3-dihydro-1-methyl-indole with an aryl-aldehyde such as 5-bromoveratraldehyde and malononitrile in the presence of a base such as piperidine produced the substituted 8,9-dihydro-7-methyl-pyrrolo[2,3-h]chromene.

Compounds of Formula I also can be prepared as illustrated by exemplary reaction in Scheme 5. The 4,7,10,13,16,19-Docosahexaenoic acid (DHA) ester of 7-hydroxymethyl-pyrrolo[2,3-h]chromene was prepared by coupling of DHA with 2-amino-4-(3-bromo-4,5-dimethoxyphenyl)-3-cyano-7-hydroxymethyl-4H-pyrrolo[2,3-h]chromene in the presence of coupling agents such as 4-dimethylaminopyridine and 1,3-dicyclohexylcarbodimide.

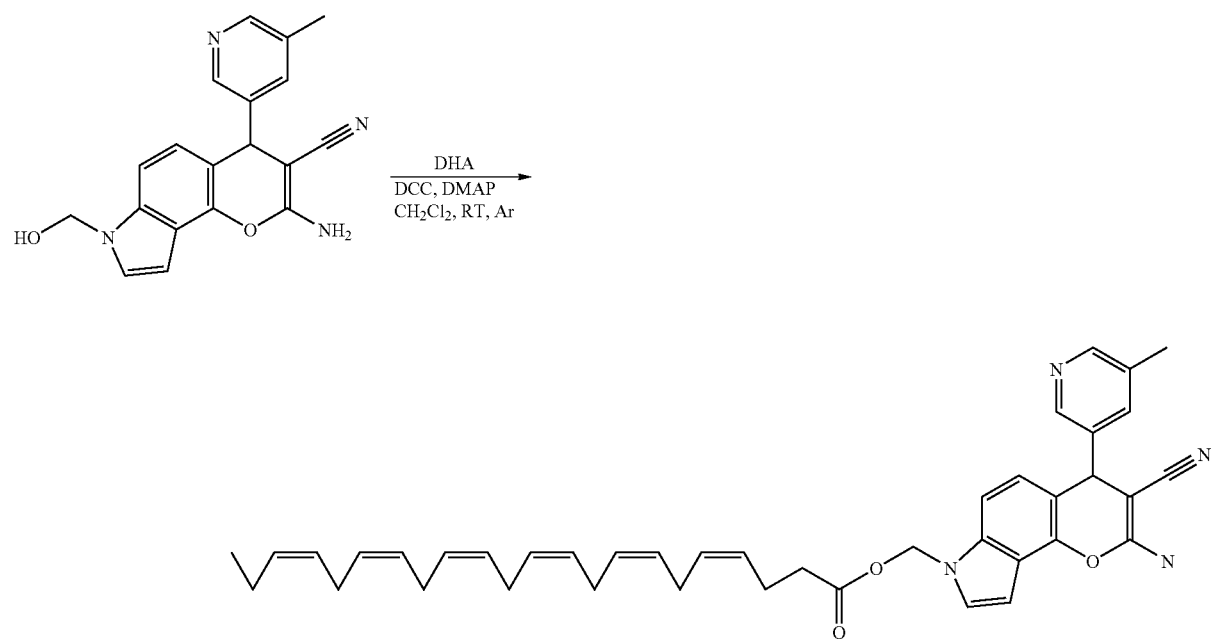

An important aspect of the present invention is the discovery that compounds having Formulae I-IV are activators of caspases and inducers of apoptosis. Therefore, these compounds are useful in a variety of clinical conditions in which there is uncontrolled cell growth and spread of abnormal cells, such as in the case of cancer.

Another important aspect of the present invention is the discovery that compounds having Formulae I-IV are potent and highly efficacious activators of caspases and inducers of apoptosis in drug resistant cancer cells, such as breast and prostate cancer cells, which enables these compounds to kill these drug resistant cancer cells. In comparison, most standard anti-cancer drugs are not effective in killing drug resistant cancer cells under the same conditions. Therefore, compounds of this invention are useful for the treatment of drug resistant cancer in animals.

The present invention includes a therapeutic method useful to modulate in vivo apoptosis or in vivo neoplastic disease, comprising administering to a subject in need of such treatment an effective amount of a compound, or a pharmaceutically acceptable salt or prodrug of the compound of Formulae I-IV, which functions as a caspase cascade activator and inducer of apoptosis.

The present invention also include a therapeutic method comprising administering to an animal an effective amount of a compound, or a pharmaceutically acceptable salt or prodrug of said compound of Formulae I-IV, wherein said therapeutic method is useful to treat cancer, which is a group of diseases characterized by the uncontrolled growth and spread of abnormal cells. Such diseases include, but are not limited to, Hodgkin's disease, non-Hodkin's lymphoma, acute lymphotic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinomas, mycosis fungoides, head or neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

In practicing the therapeutic methods, effective amounts of compositions containing therapeutically effective concentrations of the compounds formulated for oral, intravenous, local and topical application, for the treatment of neoplastic diseases and other diseases in which caspase cascade mediated physiological responses are implicated, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the disease. Typically, repeated administration is required to achieve the desired amelioration of symptoms In another embodiment, a pharmaceutical composition comprising a compound, or a pharmaceutically acceptable salt of said compound of Formulae I-IV, which functions as a caspase cascade activator and inducer of apoptosis in combination with a pharmaceutically acceptable vehicle is provided.

Another embodiment of the present invention is directed to a composition effective to inhibit neoplasia comprising a compound, or a pharmaceutically acceptable salt or prodrug of said compound of Formulae I-IV, which functions as a caspase cascade activator and inducer of apoptosis, in combination with at least one known cancer chemotherapeutic agent, or a pharmaceutically acceptable salt of said agent. Examples of known anti-cancer agents which can be used for combination therapy include, but not are limit to alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites such as 5-azacytidine, 5-fluorouracil and methotrexate; DNA antimetabolites, such as 5-fluoro-2'-deoxy-uridine, ara-C, hydroxyurea and thioguanine; and antibodies, such as Herceptin® and Rituxan®. Other known anti-cancer agents which can be used for combination therapy include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine.

In practicing the methods of the present invention, the compound of the invention may be administered together with at least one known chemotherapeutic agent as part of a unitary pharmaceutical composition. Alternatively, the compound of the invention may be administered apart from the at least one known cancer chemotherapeutic agent. In one embodiment, the compound of the invention and the at least one known cancer chemotherapeutic agent are administered substantially simultaneously, i.e. the compounds are administered at the same time or one after the other, so long as the compounds reach therapeutic levels in the blood at the same time. On another embodiment, the compound of the invention and the at least one known cancer chemotherapeutic agent are administered according to their individual dose schedule, so long as the compounds reach therapeutic levels in the blood.

Another embodiment of the present invention is directed to a composition effective to inhibit neoplasia comprising a bioconjugates of said compound of Formulae I-IV, which functions as a caspase cascade activator and inducer of apoptosis, in bioconjugation with at least one known therapeutically useful antibodies, such as Herceptin® or Rituxan®, growth factors such as DGF, NGF, cytokines, such as IL-2, IL-4, or any molecule that binds to cell surface. The antibodies and other molecules will deliver compound of Formulae I-IV to its targets and make them effective anticancer agents. The bioconjugates also could enhance the anticancer effect of therapeutically useful antibodies, such as Herceptin® or Rituxan®.

Similarly, another embodiment of the present invention is directed to a composition effective to inhibit neoplasia comprising a compound or a pharmaceutically acceptable salt or prodrug of said compound of Formulae I-IV, which functions as a caspase cascade activator and inducer of apoptosis, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound, or a pharmaceutically acceptable salt or prodrug of said compound of Formulae I-IV, which functions as a caspase cascade activator and inducer of apoptosis. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms maintaining immune homeostasis. This deletion of reactive cells has been shown to be regulated by a phenomenon known as apoptosis. Autoimmune diseases have been lately identified as a consequence of deregulated cell death. In certain autoimmune diseases, the immune system directs its powerful cytotoxic effector mechanisms against specialized cells, such as oligodendrocytes in multiple sclerosis, the beta cells of the pancreas in diabetes mellitus, and thyrocytes in Hashimoto's thyroiditis (Ohsako, S. & Elkon, K. B., *Cell Death Differ.* 6:13-21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly and generalized lymphadenopathy, hypergammaglobulinemia, and autoantibody formation. (Infante, A. J., et al., *J. Pediatr.* 133:629-633 (1998) and Vaishnaw, A. K., et al., *J. Clin. Invest.* 103:355-363 (1999)). It was reported that overexpression of Bcl-2, which is a member of the bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al., *Int. J. Mol. Med.* 1:475-483 (1998)). It is therefore evident that many types of autoimmune disease are caused by defects of the apoptotic process, and one treatment strategy would be to turn on apoptosis in the lymphocytes that are causing autoimmune disease (O'Reilly, L. A. & Strasser, A., *Inflamm. Res.* 48:5-21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., (*J. Immunol.* 162:603-608 (1999)) reported that by direct injection of DNA expression vectors encoding FasL into the inflamed thyroid, the development of lymphocytic infiltration of the thyroid was inhibited and induction of infiltrating T cells death was observed. These results show that FasL expression on thyrocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt-4T cells, both of which were resistant to apoptosis induced by anti-Fas antibody in the absence of bisindolylmaleimide VIII. Potentiation of Fas-mediated apoptosis by bisindolylmaleimide VIII was reported to be selective for activated, rather than non-activated, T cells, and was Fas-dependent. Zhou, T., et al., (*Nat. Med.* 5:42-48 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore, the application of a Fas-dependent apoptosis enhancer, such as bisindolylmaleimide VIII, may be therapeutically useful for the more effective elimination of detrimental cells and inhibition of T cell-mediated autoimmune diseases. Therefore, an effective amount of a compound, or a pharmaceutically acceptable salt or prodrug of the compound of Formulae I-IV, which functions as a caspase cascade activator and inducer of apoptosis, is an effective treatment for autoimmune disease.

Psoriasis is a chronic skin disease that is characterized by scaly red patches. Psoralen plus ultraviolet A (PUVA) is a widely used and effective treatment for psoriasis vulgaris and Coven, et al., *Photodermatol. Photoimmunol. Photomed.* 15:22-27 (1999), reported that lymphocytes treated with psoralen 8-MOP or TMP plus UVA displayed DNA degradation patterns typical of apoptotic cell death. Ozawa, et al., *J. Exp. Med.* 189:711-718 (1999) reported that induction of T cell apoptosis could be the main mechanism by which 312-nm UVB resolves psoriasis skin lesions. Low doses of methotrexate may be used to treat psoriasis to restore a clinically normal skin. Heenen, et al., *Arch. Dermatol. Res.* 290:240-245 (1998), reported that low doses of methotrexate may induce apoptosis and this mode of action could explain the reduction in epidermal hyperplasia during treatment of psoriasis with methotrexate. Therefore, an effective amount of a compound, or a pharmaceutically acceptable salt or prodrug of the compound of Formulae I-IV, which functions as a caspase cascade activator and inducer of apoptosis, is an effective treatment for hyperproliferative diseases, such as psoriasis.

Synovial cell hyperplasia is a characteristic of patients with rheumatoid arthritis (RA). Excessive proliferation of RA synovial cells, as well as defective in synovial cell death, might be responsible for the synovial cell hyperplasia. Wakisaka, et al., *Clin. Exp. Immunol.* 114:119-128 (1998), found that although RA synovial cells could die via apoptosis through Fas/FasL pathway, apoptosis of synovial cells was inhibited by proinflammatory cytokines present within the synovium, and suggested that inhibition of apoptosis by the proinflammatory cytokines may contribute to the outgrowth of synovial cells, and lead to pannus formation and the destruction of joints in patients with RA. Therefore, an effective amount of a compound, or a pharmaceutically acceptable salt or prodrug of the compound of Formulae I-IV, which functions as a caspase cascade activator and inducer of apoptosis, is an effective treatment for rheumatoid arthritis.

There have been accumulation of convincing evidence that apoptosis plays a major role in promoting resolution of the acute inflammatory response. Neutrophils are constitutively programmed to undergo apoptosis, thus limiting their proinflammatory potential and leading to rapid, specific, and non-phlogistic recognition by macrophages and semi-professional phagocytes (Savill, J., *J. Leukoc. Biol.* 61:375-380 (1997)). Boirivant, et al., *Gastroenterology* 116:557-565 (1999), reported that lamina propria T cells isolated from areas of inflammation in Crohn's disease, ulcerative colitis, and other inflammatory states manifest decreased CD2 pathway-induced apoptosis, and that studies of cells from inflamed Crohn's disease tissue indicate that this defect is accompanied by elevated Bcl-2 levels. Therefore, an effective amount of a compound, or a pharmaceutically acceptable salt or prodrug of the compound of Formulae I-IV, which functions as a caspase cascade activator and inducer of apoptosis, is an effective treatment for inflammation and inflammatory bowel disease.

Compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to mammals, e.g., humans, orally at a dose of 0.0025 to 50 mg/kg, or an equivalent amount of the pharmaceutically acceptable salt thereof, per day, of the body weight of the mammal being treated for apoptosis-mediated disorders. Preferably, approximately 0.01 to approximately 10 mg/kg is orally administered to treat or prevent such disorders. For intramuscular injection, the dose is generally approximately one-half of the oral dose. For example, a suitable intramuscular dose would be approximately 0.0025 to approximately 25 mg/kg, and most preferably, from approximately 0.01 to approximately 5 mg/kg. If a known cancer chemotherapeutic agent is also administered, it is administered in an amount which is effective to achieve its intended purpose. The amounts of such known cancer chemotherapeutic agents effective for cancer are well known to those of skill in the art.

The unit oral dose may be comprised of approximately 0.01 to approximately 50 mg, preferably approximately 0.1 to approximately 10 mg of the compound of the invention. The unit dose may be administered one or more times daily as one or more tablets, each containing from approximately 0.1 to approximately 10, conveniently approximately 0.25 to 50 mg of the compound or its solvates.

In a topical formulation, the compound may be present at a concentration of approximately 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations, which can be administered orally and that can be used for the preferred type of administration, such as tablets, dragees, and capsules, and also preparations which can be administered rectally, such as suppositories, as well as suitable solutions for administration by injection or orally, contain from approximately 0.01 to 99 percent, preferably from approximately 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular apoptosis inducers of the present invention with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular apoptosis inducers of the present invention with a solution of a pharmaceutically acceptable non-toxic base, such as sodium hydroxide, potassium hydroxide, choline hydroxide, sodium carbonate, Tris, N-methyl-glucamine and the like.

The pharmaceutical compositions of the invention may be administered to any animal which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, e.g., by means of conventional mixing, granulating, dragee-making, dissolving, or lyophilizing processes. Thus, pharmaceutical preparations for oral use can be obtained by combining the active compounds with solid excipients, optionally grinding the resultant mixture and processing the mixture of granules, after adding suitable auxiliaries, if desired or necessary, to obtain tablets or dragee cores.

Suitable excipients are, in particular, fillers, such as saccharides, e.g., lactose or sucrose, mannitol or sorbitol; cellulose preparations and/or calcium phosphates, e.g., tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropymethyl-cellulose phthalate, are used. Dye stuffs or pigments may be added to the tablets or dragee coatings, e.g., for identification or in order to characterize combinations of active compound doses.

Other pharmaceutical preparations, which can be used orally, include push-fit capsules made of gelatin, as well as soft, sealed capsules made of gelatin and a plasticizer, such as glycerol or sorbitol. The push-fit capsules can contain the active compounds in the form of granules, which may be mixed with fillers, such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, e.g., suppositories, which consist of a combination of one or more of the active compounds with a suppository base. For example, suitable suppository bases are natural or synthetic triglycerides, or paraffin hydrocarbons. In addition, it is also possible to use gelatin rectal capsules, which consist of a combination of the active compounds with a base. Possible base materials include, e.g., liquid triglycerides, polyethylene glycols, or paraffin hydrocarbons.

Suitable formulations for parenteral administration include aqueous solutions of the active compounds in water-soluble form, e.g., water-soluble salts and alkaline solutions. In addition, suspensions of the active compounds as appropriate oily injection suspensions may be administered. Suitable lipophilic solvents or vehicles include fatty oils, e.g., sesame oil, or synthetic fatty acid esters, e.g., ethyl oleate or triglycerides or polyethylene glycol-400 (the compounds are soluble in PEG400) or cremophor, or cyclodextrins. Aqueous injection suspensions may contain substances, which increase the viscosity of the suspension include, e.g., sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included, as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil, such as almond oil, is admixed. A typical example of such a cream is one which includes approximately 40 parts water, approximately 20 parts beeswax, approximately 40 parts mineral oil and approximately 1 part almond oil.

Ointments may be formulated by mixing a solution of the active ingredient in a vegetable oil, such as almond oil with warm soft paraffin, and allowing the mixture to cool. A typical example of such an ointment is one which includes approximately 30% almond oil and approximately 70% white soft paraffin by weight.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

2-Amino-4-(5-cyano-pyridin-3-yl)-3-cyano-7-methyl-4H-pyrrolo[2,3-h]chromene a) Ethyl 5-bromonicotinate: To a white stirring suspension of 5-bromonicotinic acid (3.00 g, 14.9 mmol) in ethyl alcohol (30.0 mL) was added concentrated $H_2SO_4$ (9.0 mL) dropwise over 5 min to form a clear solution. The clear solution was then heated for 22 h, cooled to room temperature, quenched with water (30 mL) and then extracted with dichloromethane (75 mL). The organic layer was washed with 10% $Na_2CO_3$ (20 mL), water (20 mL), dried over $MgSO_4$, filtered through sintered glass and concentrated to yield 2.8 g (82%) of the title compound as a white solid.

$^1$H NMR (CDCl$_3$): 9.13 (d, J=1.7 Hz, 1H), 8.84 (d, J=2.2 Hz, 1H), 8.42 (m, J=2.2, 1.7 Hz, 2H), 4.40 (q, J=7.1 Hz, 2H), 1.43 (t, J=7.1 Hz, 3H).

b) (5-Bromo-pyridin-3-yl)-methanol: A clear solution of ethyl-5-bromonicotinate (2.80 g, 12.2 mmol) in THF (35 mL) was cooled to −78° C. and lithium aluminum hydride (LAH, 0.470 g, 12.2 mmol) was added in small portions over the next 10 min. After stirring for 1 h at −78° C., the cold bath was removed. The reaction mixture was stirred at room temperature for 2 h, quenched by the slow addition of water (5 mL), filtered through a layer of celite and washed with ethyl acetate (100 mL). The organic layer was then dried over $MgSO_4$, filtered through sintered glass and concentrated to yield 1.5 g (66%) of a yellow oil residue. The residue was purified by column chromatography (elution with EtOAC:hexanes, 1:1) and yielded 1.32 g (58%) of the title compound as a yellow oil. $^1$H NMR (CDCl$_3$): 8.48 (d, J=1.9 Hz, 1H), 8.39 (s, 1H), 7.88 (t, J=1.9 Hz, 1H), 4.69 (s, 2H).

c) (5-Cyano-pyridin-3-yl)-methanol: A yellow solution of (5-bromo-pyridin-3-yl)-methanol (1.30 g, 6.91 mmol), anhydrous DMF (27.7 mL) and copper (1) cyanide (0.92 g, 10 mmol) was heated at 170° C. for 36 h. The reaction mixture was cooled to room temperature and additional copper (I) cyanide (0.058 g, 0.65 mmol) was added to the yellow solution. The reaction flask was then heated at 170° C. for an additional 12 h. The yellow solution was cooled to room temperature, quenched with NaHCO$_3$ (120 mL), and extracted with EtOAc (3×100 mL). The combined organic extracts were dried over $MgSO_4$, filtered through sintered glass and concentrated to yield 0.502 g (54%) of a brown oil residue. The residue was purified by column chromatography (elution with EtOAC:hexanes, 1:1) and yielded 0.225 g (24%) of the title compound as a white solid. $^1$H NMR (CDCl$_3$): 8.80 (dd, J=2.20, 1.92 Hz, 2H), 8.03 (m, J=2.20, 1.92 Hz, 1H), 4.83 (d, J=4.7 Hz, 2H).

d) 5-Cyano-pyridine-3-carbaldehyde: A black suspension of (5-cyano-pyridin-3-yl)-methanol (0.070 g, 0.52 mmol), anhydrous $CH_2Cl_2$ (1.04 mL) and manganese oxide (0.181 g, 2.09 mmol) was heated to reflux and monitored by TLC. After 8 h, the reaction mixture was cooled to room temperature and additional manganese oxide (0.095 g, 1.1 mmol) was added to the reaction flask. The reaction mixture was then heated to reflux. After 18 h, the reaction was still not complete by TLC and additional manganese oxide (0.097 g, 1.1 mmol) was added to the reaction flask. After heating at 60° C. for 72 h, the reaction mixture was cooled to room temperature, diluted with EtOAc (50 mL), passed through celite and washed with additional EtOAc (50 mL). The organic filtrate was dried over $MgSO_4$, filtered through sintered glass and concentrated to yield 0.064 g (93%) of a white solid. It was purified by column chromatography (elution with EtOAC:hexanes, 1:3) and yielded 0.038 g (55%) of the title compound as a white solid. $^1$H NMR (CDCl$_3$): 10.17 (s, 1H), 9.28 (d, J=1.9 Hz, 1H), 9.11 (d, J=2.2 Hz, 1H), 8.45 (dd, J=2.2, 1.9 Hz, 1H).

e) 2-Amino-4-(5-cyano-pyridin-3-yl)-3-cyano-7-methyl-4H-pyrrolo-[2,3-h]chromene: A solution of 5-cyano-pyridine-3-carbaldehyde (0.0050 g, 0.038 mmol), anhydrous EtOH (0.20 mL), 4-hydroxy-1-methyl-indole (0.0055 g, 0.038 mmol), piperidine (1.87 µL, 0.0016 mmol) and malononitrile (0.0025 g, 0.038 mmol) was stirred at room temperature for 1.5 h and then concentrated to a green residue. The residue was dissolved in EtOAc (25 mL), washed with H$_2$O (5 mL), dried over $MgSO_4$, filtered through sintered glass and concentrated to yield a yellow residue. The residue was purified by column chromatography (elution with EtOAC:hexanes, 1:1) and yielded 0.003 g (24%) of the title compound as a white solid. $^1$H NMR (Acetone-d$_6$): 8.83 (d, J=2.1 Hz, 2H), 8.09 (m, J=2.1 Hz, 1H), 7.29 (d, J=3.3 Hz, 1H), 7.18 (dd, J=8.4, 0.9 Hz, 1H), 6.83 (dd, J=8.4 Hz, 1H), 6.52 (dd, J=3.0, 0.9 Hz, 1H), 6.44 (brs, 2H), 5.10 (s, 1H), 3.83 (s, 3H).

EXAMPLE 2

2-Amino-3-cyano-7-methyl-4-(6-methyl-pyrazin-2-yl)-4H-pyrrolo[2,3-h]chromene a) 6-Methyl-pyrazine-2-carboxylic acid ethyl ester: The title compound was prepared from 6-methyl-2-pyrazinecarboxylic acid (3.00 g, 21.7 mmol) and ethyl alcohol, similar to Example 1a, yielded 1.70 g (47%) of a yellow oil. $^1$H NMR (CDCl$_3$): 9.19 (s, 1H), 8.61 (s, 1H), 4.50 (q, J=7.1 Hz, 2H), 2.69 (s, 3H), 1.47 (t, J=7.1 Hz, 3H).

b) (6-Methyl-pyrazin-2-yl)-methanol: The title compound was prepared from 6-methyl-pyrazine-2-carboxylic acid ethyl ester (1.65 g, 9.93 mmol) and lithium aluminum hydride, similar to Example 1b, and yielded 0.671 g (55%) of a brown solid. $^1$H NMR (CDCl$_3$): 8.52 (s, 1H), 8.41 (s, 1H), 4.80 (s, 2H), 2.58 (s, 3H).

c) 6-Methyl-pyrazine-2-carbaldehyde: The title compound was prepared from (6-methyl-pyrazin-2-yl)-methanol (0.672 g, 5.41 mmol), anhydrous CH$_2$Cl$_2$ (10.8 mL) and manganese oxide (1.88 g, 21.6 mmol) similar to Example 1d, and yielded 0.060 g (9%) of a yellow solid. $^1$H NMR (CDCl$_3$): 10.13 (s, 1H), 9.06 (s, 1H), 8.63 (s, 1H), 2.70 (s, 3H).

d) 2-Amino-3-cyano-7-methyl-4-(6-methyl-pyrazin-2-yl)-4H-pyrrolo[2,3-h]chromene: The title compound was prepared from 6-methyl-pyrazine-2-carbaldehyde (0.016 g, 0.13 mmol), anhydrous EtOH (0.66 mL), malononitrile (0.0086 g, 0.13 mmol), 4-hydroxy-1-methyl-indole (0.019 g, 0.13 mmol), and piperidine (6.5 µL, 0.066 mmol), similar to Example 1e, and yielded 0.030 g (72%) of a white solid: $^1$H NMR (Acetone-d$_6$): 8.47 (d, J=1.2 Hz, 1H), 8.37 (t, J=1.2, 0.6 Hz, 1H), 7.23 (d, J=3.3 Hz, 1H), 7.12 (dd, J=8.4, 0.6 Hz, 1H), 6.85 (dd, J=8.4, 0.6 Hz, 1H), 6.49 (dd, J=3.3, 1.2 Hz, 1H), 6.30 (brs, 2H), 5.02 (s, 1H), 3.81 (s, 3H), 2.47 (s, 3H).

EXAMPLE 3

2-Amino-3-cyano-7-methyl(quinoxalin-2-yl)-4H-pyrrolo[2,3-h]chromene a) Quinoxalin-2-yl-methanol: The title compound was prepared from ethyl 2-quinoxaline-carboxylate (0.200 g, 0.989 mmol) and lithium aluminum hydride similar to Example 1b, and yielded 0.0576 g (33%) of a yellow oil.

$^1$H NMR (CDCl$_3$): 8.86 (s, 1H), 8.10 (m, J=9.89 Hz, 2H), 7.77 (m, J=9.89 Hz, 2H), 5.04 (s, 2H).

b) Quinoxaline-2-carbaldehyde: The title compound was prepared from (quinoxalin-2-yl)-methanol (0.045 g, 0.26 mmol) and manganese oxide (0.090 g, 1.0 mmol), similar to Example 1d, and yielded 0.011 g (27%) of a brown solid. $^1$H NMR (CDCl$_3$): 10.30 (s, 1H), 9.44 (s, 1H), 8.25 (m, 2H), 7.94 (m, 2H).

c) 2-Amino-3-cyano-7-methyl-4-(quinoxalin-2-yl)-4H-pyrrolo[2,3-h]-chromene: The title compound was prepared from quinoxaline-2-carbaldehyde (0.0070 g, 0.044 mmol), anhydrous EtOH (0.22 mL), malononitrile (0.0029 g, 0.044 mmol), 4-hydroxy-1-methyl-indole (0.0065 g, 0.044 mmol), and piperidine (2.2 µL, 0.022 mmol) similar to Example 1e, and yielded 0.0029 g (13%) of a white solid. $^1$H NMR (Acetone-d$_6$): 8.85 (s, 1H), 8.06 (m, J=8.24, 1.65 Hz, 2H), 7.84 (m, J=7.42, 1.65 Hz, 2H), 7.29 (d, J=3.03 Hz, 1H), 7.15 (dd, J=8.52, 0.83 Hz, 1H,), 6.88 (dd, J=8.51 Hz, 1H), 6.55 (dd, J=3.29, 0.82 Hz, 1H), 6.50 (brs, 2H), 5.25 (s, 1H), 3.81 (s, 3H)

EXAMPLE 4

2-Amino-4-(3-bromo-4,5-dimethoxyphenyl)-3-cyano-7-ethyl-4H-pyrrolo[2,3-h]chromene a) 4-Benzyloxy-1-ethyl-indole: To a white suspension of sodium hydride (0.027 g, 0.67 mmol) in THF (1.35 mL) at 0° C., was added 4-benzyloxy-indole (0.150 g, 0.672 mmol) in portions over 5 min. The resultant pink mixture was allowed to warm to room temperature over 1 h and then bromoethane (0.100 mL, 1.34 mmol) was added dropwise. After stirring at room temperature for 24 h, the reaction mixture was heated at 40° C. for 18 h and then quenched with water (10 mL). The aqueous layer was extracted with ethyl acetate (2×20 mL). The extracts were dried over Na$_2$SO$_4$, filtered through sintered glass and concentrated to yield 0.235 g of a pink residue. It was purified by column chromatography (elution with EtOAC:hexanes, 1:4) to yield 0.068 g (40%) of the title compound as a white solid. $^1$H NMR (CDCl$_3$): 7.50 (m, 2H), 7.34 (m, 2H), 7.06 (m, 3H), 6.65 (dd, 1H), 6.56 (d, 1H), 5.22 (s, 2H), 4.14 (q, J=7.4 Hz, 2H), 1.44 (t, J=7.4 Hz, 3H).

b) 1-Ethyl-4-hydroxy-indole: To a brown solution of 4-benzyloxy-1-ethyl-indole (0.068 g, 0.27 mmol) and methanol (1.35 mL) in a hydrogenation apparatus par shaker flask (oven dried), was added 5% Pd/C (0.029 g, 0.27 mmol). The black mixture was then filled with hydrogen gas at 40 psi and shaken for 2 h. The reaction mixture was diluted with methanol (15 mL), filtered through a layer of celite and washed with additional warm methanol (75 mL). The organic filtrate was concentrated to yield 0.043 g (>100%) of a black oil. $^1$H NMR (CDCl$_3$) 7.01 (m, 3H), 6.54 (m, 2H), 4.15 (q, J=7.42 Hz, 2H), 1.45 (t, J=7.42 Hz, 3H).

c) 2-Amino-4-(3-bromo-4,5-dimethoxyphenyl)-3-cyano-7-ethyl-4H-pyrrolo[2,3-h]chromene: The title compound was prepared from 5-bromoveratraldehyde (0.0654 g, 0.267 mmol), anhydrous EtOH (1.33 mL), malononitrile (0.0176 g, 0.267 mmol), 1-ethyl-4-hydroxy-indole (0.043 g, 0.267 mmol), and piperidine (13.2 µL, 0.133 mmol) similar to Example 1e, and yielded 0.022 g (18%) of a white solid. $^1$H NMR (CDCl$_3$) 7.27 (m, 1H), 7.12 (d, J=3.02 Hz, 1H), 7.05 (dd, J=8.51, 0.83 Hz, 1H), 6.92 (d, J=1.92 Hz, 1H), 6.74 (m, J=1.92 Hz, 2H), 4.77 (s, 1H), 4.69 (brs, 2H), 4.14 (q, J=7.42 Hz, 2H), 3.83 (s, 3H), 3.82 (s, 3H), 1.46 (t, J=7.42 Hz, 3H).

EXAMPLE 5

2-Amino-4-(3-bromo-4,5-dimethoxyphenyl)-3-cyano-7-cyclopropylmethyl-4H-pyrrolo[2,3-h]chromene a) 4-Benzyloxy-1-cyclopropylmethyl-indole: The title compound was prepared from sodium hydride (0.027 g, 0.67 mmol), 4-benzyloxy-indole (0.150 g, 0.672 mmol) and (bromomethyl)cyclopropane (0.13 mL, 1.3 mmol), similar to Example 4a, and yielded 0.065 g (35%) of a brown solid. $^1$H NMR (CDCl$_3$): 7.50 (m, J=6.59, 1.65 Hz, 2H), 7.35 (m, J=8.52, 7.15, 1.65 Hz, 3H), 7.13 (d, J=3.3 Hz, 1H), 7.09 (d, J=7.97 Hz, 1H), 7.00 (dd, J=8.52 Hz, 1H), 6.71 (dd, J=3.3, 0.83 Hz, 1H,), 6.57 (dd, J=7.14 Hz, 1H), 5.23 (s, 2H), 3.96 (d, J=6.87 Hz, 2H), 1.26 (m, J=6.87 Hz, 1H,), 0.61 (m, 2H), 0.35 (m, 2H).

b) 1-Cyclopropylmethyl-4-hydroxy-indole: The title compound was prepared from 4-benzyloxy-cyclopropylmethyl-indole (0.065 g, 0.23 mmol) and 5% Pd/C (0.025 g, 0.23 mmol), similar to Example 4b, and yielded 0.042 g (95%) of a black oil. ¹H NMR (CDCl₃): 7.15 (d, 1H), 7.07 (dd, 1H), 6.96 (dd, 1H), 6.53 (m, 2H), 3.95 (d, 2H), 1.26 (m, 1H), 0.62 (m, 2H), 0.35 (m, 2H).

c) 2-Amino-4-(3-bromo-4,5-dimethoxyphenyl)-3-cyano-7-cyclo-propylmethyl-4H-pyrrolo[2,3-h]chromene: The title compound was prepared from 5-bromoveratraldehyde (0.052 g, 0.21 mmol), anhydrous EtOH (1.07 mL), malononitrile (0.014 g, 0.21 mmol), 1-cyclopropylmethyl-4-hydroxy-indole (0.040 g, 0.21 mmol), and piperidine (10.5 μL, 0.107 mmol), similar to Example 1e, and yielded 0.015 g (10%) of a white solid. ¹H NMR (Acetone-d₆): 7.40 (d, J=3.29 Hz, 1H), 7.25 (d, J=8.52, 0.82 Hz, 1H), 7.05 (d, J=1.92 Hz, 1H), 6.99 (d, J=1.92 Hz, 1H), 6.85 (d, J=8.52 Hz, 1H), 6.52 (dd, J=3.02, 0.83 Hz, 1H), 6.26 (brs, 2H), 4.84 (s, 1H), 3.86 (d, 2H), 3.76 (s, 6H), 1.30 (m, 1H), 0.56 (m, 2H), 0.40 (m, 2H).

EXAMPLE 6

2-Amino-4-(3-bromo-4,5-diethoxyphenyl)-3-cyano-7-(2-diethylamino-ethyl)₄H-pyrrolo[2,3-h]chromene a) [2-(4-Benzyloxy-indol-1-yl)-ethyl]-diethyl-amine: The title compound was prepared from sodium hydride (0.134 g, 3.36 mmol), 4-benzyloxy-indole (0.150 g, 0.672 mmol) and 2-bromo-N,N-diethyl-ethylamine, similar to Example 4a, and yielded 0.21 g (97%) of a yellow oil.

¹H NMR (CDCl₃) 7.48 (m, 2H), 7.35 (m, 3H), 7.10 (t, J=8.24, 7.69 Hz, 1H), 7.01 (d, J=3.02 Hz, 1H), 6.96 (d, J=8.25 Hz, 1H), 6.64 (d, J=3.02 Hz, 1H), 6.54 (d, J=7.69 Hz, 1H), 5.19 (s, 2H), 4.12 (t, J=7.42 Hz, 2H), 2.76 (t, J=7.42 Hz, 2H), 2.54 (q, J=7.14 Hz, 4H), 1.00 (t, J=7.14 Hz, 6H).

b) 1-(2-Diethylamino-ethyl)₄-hydroxy-indole: The title compound was prepared from [2-(4-benzyloxy-indol-1-yl)-ethyl]-diethyl-amine (0.210 g, 0.651 mmol) and 5% Pd/C (0.069 g, 0.65 mmol), similar to Example 4b, and yielded 0.057 g (38%) of a white solid. ¹H NMR (CDCl₃) 6.95 (m, 3H), 6.51 (m, 2H), 4.15 (q, 2H), 2.83 (m, 2H), 2.63 (m, 4H), 1.05 (t, 6H).

c) 2-Amino-4-(3-bromo-4,5-dimethoxyphenyl)-3-cyano-7-(2-diethyl-amino-ethyl)-4H-pyrrolo[2,3-h]chromene: The title compound was prepared from 5-bromoveratraldehyde (0.0316 g, 0.129 mmol), anhydrous EtOH (0.65 mL), malononitrile (0.0085 g, 0.13 mmol), 1-(2-diethylamino-ethyl)₄ hydroxy-indole (0.017 g, 0.13 mmol), and piperidine (6.4 μL, 0.064 mmol), similar to Example 1e, and yielded 0.007 g (10%) of a white solid. ¹H NMR (CDCl₃): 7.15 (d, J=3.29 Hz, 1H), 7.05 (dd, J=8.52, 0.83 Hz, 1H), 6.91 (d, J=2.2 Hz, 1H), 6.75 (m, 2H), 6.55 (dd, J=3.29 Hz, 1H), 4.77 (s, 1H), 4.70 (brs, 2H), 4.15 (t, J=7.42 Hz, 2H), 3.83 (s, 6H), 2.78 (t, J=7.42 Hz, 211), 2.55 (q, J=7.14 Hz, 4H), 0.98 (t, J=7.15 Hz, 6H).

EXAMPLE 7

2-Amino-4-(5-chloro-pyridin-3-yl)-3-cyano-7-methyl-4H-pyrrolo[2,3-h]chromene a) 5-Chloro-pyridine-3-carbaldehyde: To a solution of oxalyl chloride (2.0 M solution in CH₂Cl₂, 30.0 mL, 60.0 mmol) in anhydrous CH₂Cl₂ (20.0 mL) cooled at 0° C., was added anhydrous DMF (3.0 mL, 38 mmol) dropwise, resulting in a white precipitate. The ice bath was removed and the white suspension was allowed to warm to room temperature. The white precipitate was filtered and collected on a sintered glass funnel.

To a suspension of the above white precipitate (0.487 g, 3.81 mmol) in anhydrous acetonitrile (5.86 mL) and anhydrous THF (11.91 mL) at −55° C. was added pyridine (0.043 mL, 0.53 mmol) and 5-chloronicotinic acid (0.200 g, 1.27 mmol). The white suspension was warmed to room temperature over the next 3 h and then cooled to −78° C. While maintaining the internal temperature below −70° C., CuI (0.010 g) was added followed by the dropwise addition of LiAlH(t-BuO)₃ (1.0 M solution in THF, 0.646 g, 2.54 mmol). The internal temperature was maintained below −70° C. for an additional 0.5 h and then the reaction was quenched with 2.0 N HCl (3 mL). The suspension was warmed to room temperature and diluted with ethyl acetate (150 mL), dried over Na₂SO₄, filtered through sintered glass and concentrated to a brown residue. The residue was purified by column chromatography (elution with EtOAC:hexanes, 1:4), and yielded 0.0484 g (27%) of the title compound as a white solid. ¹H NMR (CDCl₃): 10.11 (s, 1H), 8.95 (d, J=1.93 Hz, 1H), 8.81 (d, J=2.47 Hz, 1H), 8.15 (dd, J=2.47, 1.93 Hz, 1H).

b) 2-Amino-4-(5-chloro-pyridin-3-yl)-3-cyano-7-methyl-4H-pyrrolo-[2,3-h]chromene: The title compound was prepared from 5-chloro-pyridine-3-carbaldehyde (0.0017 g, 0.12 mmol), anhydrous EtOH (0.60 mL), malononitrile (0.0080 g, 0.12 mmol), 4-hydroxy-1-methyl-indole (0.0018 g, 0.12 mmol), and piperidine (6.0 μL, 0.060 mmol), similar to Example 1e, and yielded 0.025 g (62%) of a white solid. ¹H NMR (Acetone-4): 8.52 (d, J=1.92 Hz, 1H), 8.44 (d, J=2.20 Hz, 1H), 7.65 (t, J=2.2 Hz, 1H), 7.27 (d, J=3.3 Hz, 1H), 7.18 (dd, J=8.52, 0.83 Hz, 1H), 6.82 (d, J=8.51 Hz, 1H), 6.52 (dd, J=3.02, 0.83 Hz, 1H), 6.38 (brs, 2H), 5.01 (s, 1H), 3.83 (s, 3H).

EXAMPLE 8

2-Amino-3-cyano-4-(indol-3-yl)-7-methyl-4H-pyrrolo[2,3-h]chromene a) 2-(Indol-3-ylmethylene)-malononitrile: A yellow suspension of malononitrile (0.114 g, 1.72 mmol), anhydrous EtOH (1.72 mL), indole-3-carboxaldehyde (0.250 g, 1.72 mmol), and piperidine (6.8 μL, 0.069 mmol) was heated to form a yellow solution. Within 5 min, a yellow precipitate was formed and the reaction mixture was cooled to room temperature over 15 min. The yellow precipitate was filtered and collected, yielding 0.250 g (75%) of the title compound as a yellow solid.

b) 2-Amino-3-cyano-4-(indol-3-yl)-7-methyl-4H-pyrrolo-[2,3-h]-chromene: A yellow solution of 2-(1H-indol-3-ylmethylene)-malononitrile (0.100 g, 0.517 mmol), anhydrous EtOH (2.0 mL), 4-hydroxy-1-methyl-indole (0.076 g, 0.52 mmol), and piperidine (51 μL, 0.52 mmol) was stirred at room temperature for 4 h, diluted with EtOAc (25 mL), and concentrated to yield a brown residue. The residue was purified by column chromatography (elution with EtOAC:hexanes, 1:1), and yielded 0.092 g (52%) of the title compound as a white solid. ¹H NMR (Acetone-d₆): 8.52 (d, J=1.92 Hz, 1H), 8.44 (d, J=2.20 Hz, 1H), 7.65 (t, J=2.2 Hz, 1H), 7.27 (d, J=3.3 Hz, 1H), 7.18 (dd, 8.52, 0.83 Hz, 1H), 6.82 (d, J=8.51 Hz, 1H), 6.52 (dd, J=3.02, 0.83 Hz, 1H), 6.38 (brs, 2H), 5.01 (s, 1H), 3.83 (s, 3H).

EXAMPLE 9

2-Amino-4-(5-chloro-6-hydroxy-pyridin-3-yl)-3-cyano-7-methyl-4H-pyrrolo[2,3-h]chromene a) 5-Chloro-6-hydroxy-pyridine-3-carbaldehyde: The title compound was prepared from 5-chloro-6-hydroxynicotinic acid (1.00 g, 5.76 mmol) and Li(t-BuO)₃AlH (1.0 M solution in TBF, 11.5 mL, 11.5 mmol), similar to Example 4a, yielded 0.397 g (44%) of a white solid. $^1$H NMR (DMSO-d$_6$): 9.61 (s, 1H), 8.32 (d, J=1.1 Hz, 1H), 7.98 (d, J=1.92 Hz, 1H).

b) 2-(5-Chloro-6-hydroxy-pyridin-3-ylmethylene)-malononitrile: The title compound was prepared from 5-chloro-6-hydroxy-pyridine-3-carbaldehyde (0.170 g, 1.08 mmol), anhydrous EtOH (1.00 mL), malononitrile (0.071 g, 1.08 mmol), and piperidine (4.3 µL, 0.043 mmol), similar to Example 8a, and yielded 0.130 g (59%) of a brown solid. $^1$H NMR (DMSO-d$_6$): 8.31 (d, 1H), 8.21 (s, 1H), 8.13 (s, 1H).

c) 2-Amino-4-(5-chloro-6-hydroxy-pyridin-3-yl)-3-cyano-7-methyl-4H-pyrrolo[2,3-h]chromene: A brown suspension 2-(5-chloro-6-hydroxy-pyridin-3-ylmethylene)-malononitrile (0.112 g, 0.544 mmol), anhydrous EtOH (2.2 mL), 4-hydroxy-1-methyl-indole (0.080 g, 0.54 mmol), and piperidine (54 µL, 0.54 mmol) was heated at 90° C. for 2 h, stirred at room temperature for 17 h, diluted with EtOAc (5 mL), and concentrated to yield a brown residue. The residue was washed with EtOAC:hexanes, 1:1, and MeOH to remove impurities, yielding 0.130 g (68%) of the title compound as a brown solid. $^1$H NMR (DMSO-d$_6$): 7.40 (d, 1H), 7.35 (d, J=3.02 Hz, 1H), 7.31 (d, J=2.47 Hz, 1H), 7.20 (d, J=8.52 Hz, 1H), 7.02 (brs, 2H), 6.78 (d, J=8.24 Hz, 1H), 6.43 (d, J=3.02 Hz, 1H), 4.71 (s, 1H), 3.77 (s, 3H).

EXAMPLE 10

2-Amino-3-cyano-4-(5-methyl-pyridin-3-yl)-7-methyl-4H-pyrrolo[2,3-h]chromene

To a solution of 5-methyl-pyridine-3-carbaldehyde (121 mg, 1 mmol) and 4-hydroxy-1-methyl-indole (146 mg, 0.99 mmol) in absolute ethanol (5 mL) at 0° C., was added malononitrile (67 mg, 1.01 mmol) and piperidine (0.1 mL). The clear solution was slowly warmed to room temperature and stirred overnight. The product was collected by vacuum filtration, washed with ethanol, and dried in vacuo as a yellow powder (269 mg, 86%). $^1$H NMR (CDCl$_3$): 8.34 (d, J=2.1 Hz, 1H), 8.31 (dd, J=0.6, 2.1 Hz, 1H), 7.29 (m, 1H), 7.06 (d, J=3.0 Hz, 1H), 7.02 (dd, J=0.9, 8.4 Hz, 1H), 6.72 (d, J=8.4 Hz, 1H), 6.57 (dd, J=0.9, 3.0 Hz, 1H), 4.85 (s, 1H), 4.72 (brs, 2H), 3.77 (s, 3H), 2.27 (s, 3H).

EXAMPLE 11

2-Amino-4-(5-bromo-pyridin-3-yl)-3-cyano-7-methyl-4H-pyrrolo [2,3-h]chromene

The title compound was prepared from 5-bromo-pyridine-3-carbaldehyde (44 mg, 0.24 mmol), 4-hydroxy-1-methyl-indole (35 mg, 0.24 mmol), malononitrile (16 mg, 0.24 mmol) and piperidine (0.05 mL), similar to Example 10, and isolated as a solid. $^1$H NMR (CDCl$_3$): 8.54 (d, J=2.4 Hz, 1H), 8.47 (d, J=1.8 Hz, 1H), 7.60 (m, 1H), 7.08 (d, J=3.0 Hz, 1H), 7.05 (d, J=8.4 Hz, 1H), 6.70 (d, J=8.7 Hz, 1H), 6.58 (d, J=3.0 Hz, 1H), 4.89 (s, 1H), 4.78 (brs, 2H), 3.79 (s, 3H).

EXAMPLE 12

2-Amino-4-(3-bromo-4,5-dimethoxyphenyl)-3-cyano-7-methyl-4H-imidazo[4,5-h]chromene a) 4-Nitrobenzooxazole: A mixture of 2-amino-3-nitrophenol (7.868 g, 51.0 mmol), triethyl orthformate (9.320 g, 62.9 mmol) and p-toluenesulfonic acid (0.30 g, 1.58 mmol) was heated at 120° C. After 5 h, approximately 8.5 mL of ethyl alcohol was collected using Dean-Stack distillation head. The reaction mixture was then evaporated and dried further in vacuo to yield a dark solid. $^1$H NMR (CDCl$_3$): 8.36 (s, 1H), 8.26 (dd, J=0.9, 8.4 Hz, 1H), 7.96 (dd, J=0.9, 8.4 Hz, 1H), 7.58 (t, J=8.1 Hz, 1H).

b) 4-Aminobenzooxazole: The above crude 4-nitrobenzooxazole and Pd/C (5%, 0.51 g) were suspended in MeOH (50 mL). The mixture was shaken under H$_2$ (50 psi) at room temperature overnight. The mixture was filtered through a layer of celite, washed with MeOH. The solvent was evaporated under reduced pressure to yield 6.87 g (100%) as a light brown solid. $^1$H NMR (CDCl$_3$): 7.96 (s, 1H), 7.16 (t, J=8.1 Hz, 1H), 6.95 (dd, J=0.9, 8.1 Hz, 1H), 6.61 (dd, J=0.6, 8.1 Hz, 1H), 4.33 (brs, 2H).

c) 4-(Aminomethylene-1'-benzotriazolyl)benzooxazole: 1H-benzo-triazole-1-methanol was added to a stirred 4-aminobenzooxazole (6.874 g, 51 mmol) solution in absolute ethanol (85 mL). The suspension was stirred at room temperature overnight. The solid was collected by filtration, washed with ethanol, and dried in vacuo to yield 10.681 g (79%) as an off-white solid. $^1$H NMR (CDCl$_3$): 8.04 (d, J=8.4 Hz, 1H), 7.98 (s, 1H), 7.70 (d, J=8.4 Hz, 1H), 7.45 (dt, J=1.2, 6.9 Hz, 1H), 7.35 (dt, J=0.9, 6.9 Hz, 1H), 7.21 (t, J=8.4 Hz, 1H), 7.00 (dd, J=0.6, 8.4 Hz, 1H), 6.93 (d, J=8.1 Hz, 1H), 6.34 (d, J=7.2 Hz, 2H), 5.85 (t, J=6.6 Hz, 1H).

d) 4-Hydroxy-1-methylbenzimidazole: To a stirred suspension of 4-(aminomethylene-1'-benzotriazolyl)benzooxazole (223 mg, 0.84 mmol) in absolute ethanol (10 mL) was added sodium borohydride (110 mg, 2.91 mmol) portionwise (three portions) over 4 h period. The reaction mixture was then stirred overnight. To the reaction mixture was added 21% sodium ethoxide solution in ethanol (5 mL) and ethanol (10 mL). The mixture was stirred for two days at room temperature. The mixture was diluted with water (10 mL), neutralized to pH=7 with 2M hydrochloric acid, and extracted with methylene chloride (3×20 mL). The methylene chloride solution was washed with brine (10 mL), dried over MgSO$_4$, and evaporated under reduced pressure to yield a dark oily residue. It was purified by column chromatography (silica gel, EtOAC:hexanes, 1:3, 1:2, then 100% EtOAc) to yield 62 mg (50%) of the product as a light brown solid. $^1$H NMR (CDCl$_3$): 7.89 (s, 1H), 7.24 (t, J=8.1 Hz, 1H), 6.91 (dd, J=0.6, 8.1 Hz, 1H), 6.84 (dd, J=0.9, 7.8 Hz, 1H), 3.83 (s, 3H), 2.17 (s, 1H).

e) 2-Amino-4-(3-bromo-4,5-dimethoxyphenyl)-3-cyano-7-methyl-4H-imidazo[4,5-h]chromene: The title compound was prepared from 5-bromoveratraldehyde (141 mg, 0.57 mmol), 4-hydroxy-1-methylbenzimidazole (85 mg, 0.57 mmol), malononitrile (38 mg, 0.57 mmol) and piperidine (0.1 mL), similar to Example 10 and isolated as a light brown solid (110 mg, 43%): $^1$H NMR (CDCl$_3$): 7.88 (s, 1H), 7.11 (d, J=8.4 Hz, 1H), 6.92 (d, J=1.8 Hz, 1H), 6.90 (d, J=8.7 Hz, 1H), 6.72 (d, J=2.1 Hz, 1H), 4.84 (brs, 2H), 4.80 (s, 1H), 3.85 (s, 3H), 3.83 (s, 3H), 3.81 (s, 1H).

EXAMPLE 13

2-Amino-4-(5-bromo-pyridin-3-yl)-3-cyano-7-methyl-4H-imidazo[4,5-h]chromene

The title compound was prepared from 5-bromo-pyridine-3-carbaldehyde (45 mg, 0.242 mmol), 4-hydroxy-1-methyl-benzimidazole (26 mg, 0.175 mmol), malononitrile (13 mg, 0.197 mmol) and piperidine (0.1 mL), similar to Example 10, and isolated as an off-white solid (33 mg, 49%). $^1$H NMR (DMSO-d$_6$): 8.59 (d, J=2.1 Hz, 1H), 8.49 (d, J=1.8 Hz, 1H), 8.22 (s, 1H), 7.80 (t, J=2.1 Hz, 1H), 7.32 (d, J=8.1 Hz, 1H), 7.23 (brs, 2H), 6.90 (d, J=8.4 Hz, 1H), 5.03 (s, 1H), 3.81 (s, 3H).

EXAMPLE 14

2-Amino-3-cyano-4-(5-methyl-pyridin-3-yl)-7-methyl-4H-imidazo[4,5-h]chromene

The title compound was prepared from 5-methyl-pyridine-3-carbaldehyde (25 mg, 0.21 mmol), 4-hydroxy-1-methyl-benzimidazole (26 mg, 0.18 mmol), malononitrile (12 mg, 0.18 mmol) and piperidine (0.1 mL), similar to Example 10, and isolated as an off-white solid (25 mg, 45%). $^1$H NMR DMSO-$d_6$): 8.32 (d, J=2.1 Hz, 1H), 8.27 (d, J=1.8 Hz, 1H), 8.20 (s, 1H), 7.32 (m, 1H), 7.28 (d, J=8.4 Hz, 1H), 7.12 (brs, 2H), 6.86 (d, J=8.4 Hz, 1H), 4.91 (s, 1H), 3.80 (s, 3H), 2.23 (s, 3H).

EXAMPLE 15

4-Hydroxy-1-methyl-indole

Method a:

A solution of 4-methoxy-1-methylindole (500 mg, 3.1 mmol) and 1M BBr$_3$/CH$_2$Cl$_2$ (8 mL, 8 mmol) in 10 mL CH$_2$Cl$_2$ was stirred at room temperature overnight. The solution was poured into NaHCO$_3$ saturated solution (20 mL). The organic layer was separated, washed with brine and dried over Na$_2$SO$_4$. The solvent was removed in vacuo. The crude material was purified by flash column chromatography (6:1, hexane; ethyl acetate) to yield 132 mg (29%) of the title compound. $^1$H NMR (CDCl$_3$): 7.09-7.04 (m, 1H), 6.96-6.90 (m, 2H), 6.52-6.49 (m, 2H), 5.32 (brs, 1H), 3.73 (s, 3H).

Method b:

a) 4-Benzyloxy-1-methyl-indole: To a white suspension of sodium hydride (0.089 g, 2.24 mmol) and DMF (4.50 mL) was added 4-benzyloxy-indole (0.500 g, 2.24 mmol) in portions over 5 min. The resultant brown mixture was allowed to warm to room temperature over 1 h and then iodomethane (0.28 mL, 4.5 mmol) was added dropwise. After stirring at room temperature for 5 h, and additional 2 equivalents of iodomethane (0.28 mL, 4.5 mmol) was added to the brown mixture. The reaction mixture was stirred for 1 h, then quenched with water (10 mL) and extracted with ethyl acetate (2×20 mL). The extracts were dried over Na$_2$SO$_4$, filtered through sintered glass and concentrated to yield 0.607 g (>100%) of a brown oil residue. The residue was purified by column chromatography (elution with EtOAC:hexanes, 1:4) to yield 0.253 g (47%) of the title compound as a brown residue. $^1$H NMR (CDCl$_3$): 7.48 (m, 2H), 7.35 (m, 3H), 7.10 (t, 1H), 6.92 (m, 2H), 6.63 (dd, 1H), 6.55 (dd, 1H), 5.19 (s, 2H), 3.68 (s, 3H).

b) 4-Hydroxy-1-methyl-indole: To a brown solution of 4-benzyloxy-1-methylindole (0.250 g, 1.12 mmol) and methanol (2.25 mL) in a hydrogenation apparatus par shaker flask (oven dried) was added 5% Pd/C (0.119 g, 1.12 mmol). The black mixture was attached to a hydrogenation apparatus and degassed (3×), then filled with hydrogen gas. After the final degassing, the par shaker flask was filled with hydrogen gas at 40 psi and shaken for 16 h. The reaction product was diluted with methanol (15 mL), filtered through a layer of celite (2.5 in d×2 in h) and washed with additional warm methanol (75 mL). The organic filtrate was concentrated to yield 0.160 g (97%) of a black oil. $^1$H NMR (CDCl$_3$): 7.07 (t, J=8.24 Hz, 1H), 6.92 (m, J=8.24 Hz, 2H), 6.52 (m, J=2.47 Hz, 2H), 4.60 (brs, 1H), 3.75 (s, 3H).

EXAMPLE 16

2-Amino-4-(3-bromo-4,5-dimethoxyphenyl)-3-cyano-7-methyl-4H-pyrrolo[2,3-h]chromene To a solution of 4-hydroxy-1-methyl-indole (132 mg, 0.90 mmol), 5-bromoveratraldehyde (220 mg, 0.90 mmol) and malononitrile (59.3 mg, 0.90 mmol) in ethanol (3 mL) was added piperidine (0.05 mL, 0.45 mmol). The solution was stirred at room temperature for 2 h and precipitates were observed. The precipitates were collected by filtration and dried to yield 260 mg (66%) of title compound as a white solid. $^1$H NMR (CDCl$_3$): 7.07-7.02 (m, 2H), 6.91(d, J=2.1 Hz, 1H), 6.77-6.75 (m, 2H), 6.57 (dd, J=0.9 Hz, 1H), 4.78 (s, 1H), 4.70 (brs, 2H), 3.82 (s, 6H), 3.78 (s, 3H).

EXAMPLE 17

2-Amino-4-(3-bromo-4,5-dimethoxyphenyl)-3-cyano-7-hydroxymethyl-4H-pyrrolo[2,3-h]chromene a) 1-Hydroxymethyl-4-hydroxy-indole: A solution of 4-benzyloxyindole (1.0 g, 4.48 mmol), formaldehyde (2.0 mL, 26.8 mmol) and 2 N NaOH (2.24 mL, 4.48 mmol) in 10 mL EtOH was stirred at the room temperature for 4 h. The solvent was removed in vacuo. The crude material was purified by flash column chromatography (3:1, hexane:ethyl acetate) to yield 1.13 g of 4-benzyloxy-1-hydroxymethylindole, which was hydrogenated by 5% Pd/C in 40 mL methanol under H$_2$ (50 psi) to yield 580 mg (79.5%) of the title compound. $^1$H NMR (CDCl$_3$): 7.15-7.07 (m, 3H), 6.60-6.55 (m, 2H), 5.62 (d, J=7.5 Hz, 2H), 4.93 (s, 1H), 2.37 (t, J=7.2 Hz, 1H).

b) 2-Amino-4-(3-bromo-4,5-dimethoxyphenyl)-3-cyano-7-hydroxy-methyl-4H-pyrrolo[2,3-h]chromene: The title compound was prepared from 1-hydroxymethyl-4-hydroxy-indole (550 mg, 3.37 mmol), 5-bromoveratraldehyde (826 mg, 3.37 mmol), malononitrile (222 mg, 3.37 mmol) and piperidine (0.17 mL, 1.7 mmol), similar to Example 16, to yield 1.15 g (75%) of a white solid. $^1$H NMR (CDCl$_3$): 7.22-7.18 (m, 2H), 6.90 (d, J=1.8 Hz, 1H), 6.81 (d, J=8.4 Hz, 1H), 6.75 (d, J=1.8 Hz, 1H), 6.64 (d, J=3.3 Hz, 1H), 5.61 (s, 21), 4.77 (s, 1M, 4.70 (brs, 2H), 3.83 (s, 31), 3.82 (s, 3H), 2.47 (brs, 1H).

EXAMPLE 18

2-Amino-4-(3-bromo-4-hydroxy-5-methoxyphenyl)-3-cyano-7-methyl-4H-pyrrolo[2,3-h]chromene a) 3-Bromo-4-hydroxy-5-methoxybenzylidene-malononitrile: To a mixture of 3-bromo-4-hydroxy-5-methoxybenzaldehyde (2.31 g, 10 mmol) and malononitrile (660, 10 mmol) in 20 mL of ethanol was added piperidine (0.5 mL, 0.5 mmol). The solution was stirred at room temperature overnight and precipitates were observed. The precipitates were collected by filtration and dried to yield 2.14 g (77%) of title compound as a red solid.

b) 2-Amino-4-(3-bromo-4-hydroxy-5-methoxyphenyl)-3-cyano-7-methyl-4H-pyrrolo[2,3-h]chromene: To a mixture of 3-bromo-4-hydroxy-5-methoxybenzylidene-malononitrile, malononitrile (607 mg, 2.18 mmol) and 4-hydroxy-1-methyl-indole (160 mg, 1.09 mmol) in 20 mL of ethanol was added piperidine (0.1 mL, 2.18 mmol). The solution was refluxed overnight then the solvent was removed in vacuo. The crude product was purified by column chromatography (1:1, hexane:ethyl acetate) to yield 4 mg (0.4%) of the title compound as a white solid. $^1$H NMR (CDCl$_3$): 7.07-7.01 (m, 2H), 6.90 (d, J=2.1 Hz, 1H), 6.75 (d, J=8.7 Hz, 1H), 6.70 (d, J=1.5 Hz, 1H), 6.57 (d, J=3.3 Hz, 1H), 5.82 (brs, 1H), 4.76 (s, 1H), 4.67 (brs, 2H), 3.86 (s, 3H), 3.78 (s, 3H).

EXAMPLE 19

2-Amino-4-(3-bromo-4,5-dimethoxyphenyl)-3-cyano-7-oxiranylmethyl-4H-pyrrolo[2,3-h]chromene a) 1-Oxiranylmethyl-4-hydroxy-indole: A mixture of 4-benzyloxyindole (223 mg, 1.0 mmol), 2-bromomethyl-oxirane (168 mg, 1.2 mmol) and 60% sodium hydride (60 mg, 1.5 mmol) in 5 mL THF was refluxed overnight. The solution was poured into NaHCO$_3$ saturated solution (20 mL) and extracted with EtOAc. The organic layer was separated, washed with brine and dried over Na$_2$SO$_4$. The solvent was removed in vacuo. The crude material was purified by column chromatography (1:4, hexane:ethyl acetate) to yield 200 mg of 4-benzyloxy-1-oxiranylmethylindole, which was hydrogenated by 5% Pd/C in 20 mL methanol under H$_2$ (50 psi) to yield 70 mg (37%) of the title compound. $^1$H NMR (CDCl$_3$): 7.10-7.03 (m, 2H), 6.95 (d, J=8.4 Hz, 1H), 6.56 (dd, J=0.9 Hz, J=3.3 Hz, 1H), 6.51 (dd, J=0.9 Hz, J=7.8 Hz, 1H), 4.40-4.34 (m, 1H), 4.17-4.10 (m, 1H), 3.29-3.26 (m, 1H), 2.81-2.78 (m, 1H), 2.46-2.44 (m, 1H).

b) 2-Amino-4-(3-bromo-4,5-dimethoxyphenyl)-3-cyano-7-oxiranyl-methyl-4H-pyrrolo[2,3-h]chromene: The title compound was prepared from 1-oxiranylmethyl-4-hydroxyindole (70 mg, 0.37 mmol), 5-bromoveratraldehyde (91 mg, 0.37 mmol), malononitrile (25 mg, 0.37 mmol) and piperidine (0.01 mL, 0.18 mmol), similar to Example 16, to yield 80 mg (45%) of a white solid. $^1$H NMR (CDCl$_3$): 7.15 (dd, J=1.5 Hz, 1H), 7.10 (dd, J=2.7 Hz, 1H), 6.92-6.91 (m, 1H), 6.78-6.75 (m, 2H), 6.62 (dd, J=0.9 Hz, 1H), 4.77 (s, 1H), 4.70 (brs, 2H), 4.48-4.43 (m, 1H), 4.15-4.13 (m, 1H), 3.83 (s, 3H), 3.82 (s, 3H), 3.28-3.27 (m, 1H), 2.84-2.81 (m, 1H), 2.48-2.44 (m, 1H).

EXAMPLE 20

2-Amino-3-cyano-4-(5-methyl-pyridin-3-yl)-7-hydroxymethyl-4H-pyrrolo[2,3-h]chromene The title compound was prepared from 1-hydroxymethyl-4-hydroxy-indole (163 mg, 1.0 mmol), 5-methyl-pyridine-3-carbaldehyde (121 mg, 1.0 mmol), malononitrile (66 mg, 1.0 mmol) and piperidine (0.05 mL, 0.5 mmol), similar to Example 16, to yield 230 mg (69%) of a white solid. $^1$H NMR (DMSO-d$_6$): 8.31 (d, J=2.4 Hz, 1H), 8.27 (d, J=1.8 Hz, 1H), 7.44 (d, J=3.0 Hz, 1H), 7.31-7.26 (m, 2H), 7.01 (brs, 2H), 6.73 (d, J=8.4 Hz, 1H), 6.48-6.47 (m, 2H), 5.47 (d, J=6.0 Hz, 2H), 4.86 (s, 1H), 2.23 (s, 3H).

EXAMPLE 21

2-Amino-4-(5-bromo-pyridin-3-yl)-3-cyano-7-hydroxymethyl-4H-pyrrolo[2,3-h]chromene The title compound was prepared from 1-hydroxymethyl-4-hydroxy-indole (66 mg, 0.4 mmol), 5-bromo-pyridine-3-carbaldehyde (75 mg, 0.4 mmol), malononitrile (27 mg, 0.4 mmol) and piperidine (0.02 mL, 0.2 mmol), similar to Example 16, to yield 60 mg (38%) of a white solid. $^1$H NMR (DMSO-d$_6$): 8.58 (d, J=2.1 Hz, 1H), 8.48 (d, J=1.5 Hz, 1H), 7.78-7.76 (m, 1H), 7.45 (d, J=3.0 Hz, 1H), 7.31 (d, J=8.4 Hz, 1H), 7.11 (brs, 2H), 6.77 (d, J=8.7 Hz, 1H), 6.49 (d, J=3.3 Hz, 2H), 5.49 (brs, 2H), 4.98 (s, 1H).

EXAMPLE 22

2-Amino-4-(4-acetoxy-3-bromo-5-methoxyphenyl)-3-cyano-7-methyl-4H-pyrrolo[2,3-h]chromene To a mixture of 2-bromo-4-formyl-6-methoxyphenyl acetate (273 mg, 1 mmol) and malononitrile (66 mg, 1 mmol) in 10 mL of ethanol was added 4-hydroxy-1-methylindole (147 mg, 1 mmol) and the solution was stirred at room temperature overnight. The solvent was removed in vacuo. The crude material was purified by column chromatography (2:1, hexane:ethyl acetate) to yield 25 mg (5.3%) of the title compound $^1$H NMR (CDCl$_3$): 7.07-7.04 (m, 2H), 6.92 (s, 1H), 6.79-6.77 (m, 2H), 6.57 (s, 1H), 4.81 (s, 1H), 4.70 (s, 2H), 3.79 (s, 6H), 2.34 (s, 3H).

EXAMPLE 23

2-Amino-4-(3-bromo-4,5-dimethoxyphenyl)-3-cyano-8,9-dihydro-7-methyl-4H-pyrrolo[2,3-h]chromene a) 4-Hydroxy-2,3-dihydro-1-methylindole: 4-hydroxy-1-methylindole (410 mg, 2.79 mmol) was hydrogenated by 5% Pd/C in 20 mL methanol and 0.28 mL of con. aqueous HCl under H$_2$ to yield 120 mg (29%) of the title compound. $^1$H NMR (CDCl$_3$): 6.98 (t, J=8.5 Hz, 1H), 6.19-6.12 (m, 2H), 4.51 (s, 1H), 3.34 (t, J=8.4 Hz, 2H), 2.90 (t, J=8.7 Hz, 2H), 2.75 (s, 3H).

b) 2-Amino-4-(3-bromo-4,5-dimethoxyphenyl)-3-cyano-8,9-dihydro-7-methyl-4H-pyrrolo[2,3-h]chromene: To a mixture of 5-bromoveratraldehyde (36 mg, 0.15 mmol), 4-hydroxy-2,3-dihydro-1-methylindole (22 mg, 0.15 mmol) and malononitrile (10 mg, 0.15 mmol) in 2 mL of ethanol was added piperidine (0.01 ml, 0.1 mmol). The solution was stirred at room temperature for 5 h and precipitates were observed. The precipitates were collected by filtration and dried to yield 17 mg (26%) of title compound as white solids. $^1$H NMR (CDCl$_3$): 6.88 (s, 1H), 6.72 (s, 1H), 6.67 (d, J=8.4 Hz, 1H), 6.20 (d, J=8.4 Hz, 1H), 4.60-4.57 (m, 3H), 3.85 (s, 3H), 3.82 (s, 3H), 3.40 (t, J=8.1 Hz, 2H), 2.98 (t, J=8.7 Hz, 2H), 2.74 (s, 3H).

EXAMPLE 24

2-Amino-3-cyano-4-(3,4,5-trimethoxyphenyl)-7-methyl-4H-pyrrolo[2,3-h]chromene

To a mixture of 3,4,5-trimethoxybenzaldehyde (53 mg, 0.27 mmol), 4-hydroxy-1-methylindole (40 mg, 0.27 mmol) and malononitrile (18 mg, 0.27 mmol) in 1.5 mL of ethanol was added piperidine (0.01 ml, 0.1 mmol). The solution was stirred at room temperature overnight and precipitates were observed. The precipitates were collected by filtration and dried to yield 70 mg (66%) of title compound as white solids. $^1$H NMR (CDCl$_3$): 7.06-7.02 (m, 2H), 6.80 (d, J=8.1 Hz, 1H), 6.57 (d, J=2.4 Hz, 1H), 6.42 (s, 2H), 4.79 (s, 1H), 4.66 (s, 2H), 3.81-3.78 (m, 12H).

EXAMPLE 25

2-Amino-3-cyano-4-(3-nitrophenyl)-7-methyl-4H-pyrrolo[2,3-h]chromene

The title compound was prepared from 4-hydroxy-1-methylindole (40 mg, 0.27 mmol), 3-nitrobenzaldehyde (41 mg, 0.27 mmol) and malononitrile (18 mg, 0.27 mmol) similar to Example 24 to yield 61 mg (65%) of white solids. $^1$H NMR (CDCl$_3$): 8.10 (d, J=7.8 Hz, 1H), 8.05-8.04 (m, 1H), 7.62 (d, J=7.8 Hz, 1H), 7.49 (t, J=7.8 Hz, 1H), 7.08-7.02 (m, 2H), 6.69 (d, J=8.7 Hz, 1H), 6.59 (d, J=3.0 Hz, 1H), 5.00 (s, 1H), 4.76 (s, 2H), 3.78 (s, 3H).

EXAMPLE 26

2-Amino-3-cyano-4-(3,5-dimethoxyphenyl)-7-methyl-4H-pyrrolo[2,3-h]chromene

The title compound was prepared from 4-hydroxy-1-methylindole (40 mg, 0.27 mmol), 3,5-dimethoxybenzaldehyde (45 mg, 0.27 mmol) and malononitrile (18 mg, 0.27 mmol) similar to Example 24 to yield 62 mg (60%) of white solids. $^1$H NMR (CDCl$_3$): 7.04-7.00 (m, 2H), 6.81 (d, J=8.4 Hz, 1H), 6.55 (d, J=3.0 Hz, 1H), 6.37-6.31 (m, 3H), 4.77 (s, 1H), 4.64 (brs, 2H), 3.77-3.74 (m, 9H).

EXAMPLE 27

2-Amino-3-cyano-4-(3,4-methylenedioxo-5-methoxyphenyl)-7-methyl-4H-pyrrolo[2,3-h]chromene The title compound was prepared from 4-hydroxy-1-methylindole (40 mg, 0.27 mmol), myristicin aldehyde (49 mg, 0.27 mmol) and malononitrile (18 mg, 0.27 mmol) similar to Example 24 to yield 56 mg (55%) of white solids. $^1$H NMR (CDCl$_3$): 7.05-7.01 (m, 2H), 6.79 (d, J=8.4 Hz, 1H), 6.55 (d, J=3.0 Hz, 1H), 6.46 (s, 1H), 6.33 (d, J=1.2 Hz, 1H), 5.92-5.90 (m, 2H), 4.75 (s, 1H), 4.64 (brs, 2H), 3.88 (s, 3H), 3.77 (s, 3H).

EXAMPLE 28

2-Amino-3-cyano-4-(3-methoxyphenyl)-7-methyl-4H-pyrrolo[2,3-h]chromene

The title compound was prepared from 4-hydroxy-1-methylindole (40 mg, 0.27 mmol), 3-methoxybenzaldehyde (38 mg, 0.27 mmol) and malononitrile (18 mg, 0.27 mmol) similar to Example 24 to yield 64 mg (69%) of white solids. $^1$H NMR (CDCl$_3$): 7.23-7.18 (m, 1H), 7.05-7.00 (m, 2H), 6.83-6.74 (m, 4H), 6.56 (d, J=3.0 Hz, 1H), 4.81 (s, 1H), 4.64 (brs, 2H), 3.76 (s, 6H).

EXAMPLE 29

2-Amino-3-cyano-4-(3-bromophenyl)-7-methyl-4H-pyrrolo[2,3-h]chromene

The title compound was prepared from 4-hydroxy-1-methylindole (40 mg, 0.27 mmol), 3-bromobenzaldehyde (48 mg, 0.27 mmol) and malononitrile (18 mg, 0.27 mmol) similar to Example 24 to yield 79 mg (80%) of white solids. $^1$H NMR (CDCl$_3$): 7.36-7.31 (m, 2H), 7.21-7.16 (m, 2H), 7.06-7.01 (m, 2H), 6.73 (d, J=8.4 Hz, 1H), 6.57 (dd, J=3.0 Hz, J=0.9 Hz, 1H), 4.82 (s, 1H), 4.69 (brs, 2H), 3.78 (s, 3H).

EXAMPLE 30

2-Amino-3-cyano-4-(3,5-difluorophenyl)-7-methyl-4H-pyrrolo[2,3-h]chromene

The title compound was prepared from 4-hydroxy-1-methylindole (40 mg, 0.27 mmol), 3,5-difluorobenzaldehyde (38 mg, 0.27 mmol) and malononitrile (18 mg, 0.27 mmol) similar to Example 24 to yield 38 mg (42%) of white solids. $^1$H NMR (CDCl$_3$): 7.07-7.03 (m, 2H), 6.76-6.73 (m, 3H), 6.68-6.62 (m, 1H), 6.57 (d, J=3.0 Hz, 1H), 4.83 (s, 1H), 4.72 (brs, 2H), 3.78 (s, 3H).

EXAMPLE 31

2-Amino-3-cyano-4-(4,5-dimethoxy-3-iodophenyl)-7-methyl-4H-pyrrolo[2,3-h]chromene The title compound was prepared from 4-hydroxy-1-methylindole (40 mg, 0.27 mmol), 4,5-dimethoxy-3-iodo-benzaldehyde (80 mg, 0.27 mmol) and malononitrile (18 mg, 0.27 mmol) similar to Example 24 to yield 91 mg (69%) of white solids. $^1$H NMR (CDCl$_3$): 7.19 (d, J=1.8 Hz, 1H), 7.07-7.02 (m, 2H), 6.77-6.74 (m, 2H), 6.57 (d, J=3.3 Hz, 1H), 4.76 (s, 1H), 4.69 (brs, 2H), 3.81-3.78 (m, 9H).

EXAMPLE 32

2-Amino-3-cyano-4-(3-cyanophenyl)-7-methyl-4H-pyrrolo[2,3-h]chromene

The title compound was prepared from 4-hydroxy-1-methylindole (40 mg, 0.27 mmol), 3-cyanobenzaldehyde (36 mg, 0.27 mmol) and malononitrile (18 mg, 0.27 mmol) similar to Example 24 to yield 87 mg (98%) of white solids. $^1$H NMR (CDCl$_3$): 7.53-7.39 (m, 4H), 7.08-7.03 (m, 2H), 6.68 (d, J=8.4 Hz, 1H), 6.58 (d, J=3.3 Hz, 1H), 4.90 (s, 1H), 4.74 (brs, 2H), 3.79 (s, 3H).

EXAMPLE 33

2-Amino-3-cyano-4-(3,4,5-trimethoxyphenyl)-7-hydroxymethyl-4H-pyrrolo[2,3-h]chromene The title compound was prepared from 4-hydroxy-1-hydroxymethylindole (30 mg, 0.18 mmol), 3,4,5-trimethoxybenzaldehyde (36 mg, 0.18 mmol) and malononitrile (12 mg, 0.18 mmol) similar to Example 24 to yield 63 mg (84%) of white solids. $^1$H NMR (CDCl$_3$): 7.21-7.20 (m, 2H), 6.84 (d, J=8.4 Hz, 1H), 6.64 (d, J=3.0 Hz, 1H), 6.42 (s, 2H), 5.61 (d, J=6.0 Hz, 2H), 4.78 (s, 1H), 4.67 (brs, 2H), 3.82-3.80 (m, 9H), 2.46 (brs, 1H).

EXAMPLE 34

2-Amino-3-cyano-4-(3,5-dimethoxyphenyl)-7-hydroxymethyl-4H-pyrrolo [2,3-h]chromene The title compound was prepared from 4-hydroxy-1-hydroxymethylindole (30 mg, 0.18 mmol), 3,5-dimethoxy-benzaldehyde (31 mg, 0.18 mmol) and malononitrile (12 mg, 0.18 mmol) similar to Example 24 to yield 19 mg (27%) of white solids. $^1$H NMR (CDCl$_3$): 7.20-7.15 (m, 2H), 6.85 (d, J=8.1 Hz, 1H), 6.62 (d, J=3.3 Hz, 1H), 6.36-6.32 (m, 3H), 5.60 (s, 2H), 4.76 (s, 1H), 4.64 (brs, 2H), 3.75 (s, 6H), 2.43 (brs, 1H).

EXAMPLE 35

2-Amino-3-cyano-4-(3,5-difluorophenyl)-8,9-dihydro-7-methyl-4H-pyrrolo [2,3-h]chromene The title compound was prepared from 4-hydroxy-2,3-dihydro-1-methylindole (30 mg, 0.2 mmol), 3,5-difluorobenzaldehyde (29 mg, 0.2 mmol) and malononitrile (13 mg, 0.2 mmol) similar to Example 22 to yield 20 mg (29%) of white solids. $^1$H NMR (CDCl$_3$): 6.74-6.65 (m, 4H), 6.20 (d, J=7.8 Hz, 1H), 4.62 (s, 3H), 3.40 (t, J=8.1 Hz, 2H), 2.99 (t, J=8.7 Hz, 2H), 2.74 (s, 3H).

EXAMPLE 36

2-Amino-4-(5-methyl-pyridin-3-yl)-3-cyano-7-methyl-8,9-dihydro-4H-pyrrolo[2,3-h]chromene The title compound was prepared from 4-hydroxy-2,3-dihydro-1-methylindole (0.025 g, 0.17 mmol), 5-methyl-pyridine-3-carbaldehyde (0.020 g, 0.17 mmol), and malononitrile (0.011 g, 0.17 mmol) similar to Example 22 to yield 0.017 g (32%) of a white solid. $^1$H NMR (DMSO-$d_6$): 8.31 (d, J=2.2 Hz, 1H), 8.27 (d, J=1.4 Hz, 1H), 7.37 (m, 1H), 6.71 (dd, J=8.0, 0.83 Hz, 1H), 6.25 (dd, J=8.0 Hz, 1H), 6.22 (brs, 2H), 4.68 (s, 1H), 3.36 (t, J=16.8 Hz, 2H), 2.94 (t, J=16.8 Hz, 2H), 2.70 (s, 3H).

EXAMPLE 37

2-Amino-4-(5-nitro-thiophene-2-yl)-3-cyano-7-methyl-4H-pyrrolo[2,3-h]chromene

The title compound was prepared from 5-nitrothiophene-2-carboxaldehyde, malononitrile and 4-hydroxy-1-methyl-indole similar to Example 22, yielded 0.002 g (9%) of a brown solid. $^1$H-NMR (CDCl$_3$): 7.70 (dd, J=17.0, 3.8 Hz, 1H), 7.12 (m, J=8.2, 4.1, 2.7 Hz, 2H), 6.99 (d, J=4.1 Hz, 1H), 6.91 (d, J=8.2 Hz, 1H), 6.56 (d, J=2.7 Hz, 1H), 5.14 (s, 1), 4.88 (brs, 2H), 3.80 (s, 3H).

EXAMPLE 38

4,7,10,13,16,19-Docosahexaenoic acid {2-Amino-4-(3-bromo-4,5-dimethoxy-phenyl)-3-cyano-4H-pyrrolo[2,3-h]chromene}-7-ylmethyl ester To a solution of 2-amino-4-(3-bromo-4,5-dimethoxyphenyl)-3-cyano-7-hydroxymethyl-4H-pyrrolo[2,3-h]chromene (100 mg, 0.22 mmol) in methylene chloride (5 mL) under argon were added 4-dimethylaminopyridine (27 mg, 0.22 mmol), 1,3-dicyclohexylcarbodiimide (91 mg, 0.44 mg) and 4,7,10,13,16,19-docosahexaenoic acid (DHA, 72 mg, 0.29 mmol). The reaction mixture was stirred at room temperature for 1 h. After dilution with methylene chloride, the reaction mixture was washed with saturated NH$_4$Cl aqueous, brine and dried over Na$_2$SO$_4$. The solvent was removed in vacuo. The crude material was purified by column chromatography on silica gel with ethyl acetate and hexane (1:2) as eluant, yielding 72 mg (43%) of the title compound. $^1$H NMR (CDCl$_3$): 7.28-7.25 (m, 1H), 7.20 (d, J=8.3 Hz, 1H), 6.90 (d, J=1.8 Hz, 1H), 6.81 (d, J=8.7 Hz, 1H), 6.76 (d, J=1.8 Hz, 1H), 6.63 (d, J=3.0 Hz, 1H), 6.05 (s, 2H), 5.40-5.26 (m, 12H), 4.77 (s, 1H), 4.70 (s, 2H), 3.84-3.82 (m, 6H), 2.86-2.74 (m, 10H), 2.35-2.34 (m, 4H), 2.07 (q, J=7.5 Hz, 2H), 0.97 (t, J=7.5 Hz, 3H).

EXAMPLE 39

4,7,10,13,16,19-Docosahexaenoic acid {2-Amino-3-cyano-4-(5-methyl-pyridin-3-yl)-4H-pyrrolo[2,3-h]chromene}-7-ylmethyl ester The title compound was prepared from 2-amino-4-(5-methyl-pyridin-3-yl)-3-cyano-7-hydroxymethyl-4H-pyrrolo[2,3-h]chromene (30 mg, 0.09 mmol) and 4,7,10,13,16,19-docosahexaenoic acid (30 mg, 0.12 mmol) similar to Example 38 to yield 48 mg (83%) of oil. $^1$H NMR (CDCl$_3$): 8.33-8.31 (m, 2H), 7.31-7.26 (m, 2H), 7.19 (d, J=8.7 Hz, 1H), 6.77 (d, J=8.4 Hz, 1H), 6.63 (d, J=3.3 Hz, 1H), 6.04 (s, 2H), 5.40-5.28 (m, 12H), 4.84 (s, 1H), 4.81 (s, 2H), 2.86-2.73 (m, 10H), 2.34-2.28 (m, 7H), 2.12-2.04 (m, 2H), 0.96 (t, J=7.5 Hz, 3H).

EXAMPLE 40A

2-Amino-3-cyano-4-(3-fluorophenyl)-7-methyl-4H-pyrrolo[2,3-h]chromene

To a mixture of 3-fluorobenzaldehyde (46 mg, 0.37 mmol) and malononitrile (25 mg, 0.37 mmol) in ethanol (1 mL) was added 4-hydroxy-1-methyl-indole (55 mg, 0.37 mmol) followed by piperidine (0.02 mL, 0.19 mmol, 0.5 eq.). Reaction mixture was stirred at room temperature overnight. The desired compound precipitated and was collected, washed with ethanol and dried, yielding 36 mg of a yellow solid. $^1$H NMR (CDCl$_3$): 7.28-7.23 (m, 1H), 7.05-7.01 (m, 3H), 6.92-6.86 (m, 2H), 6.74 (d, J=8.4 Hz, 1H), 6.56 (d, J=3.1 Hz, 1H), 4.84 (s, 1H), 4.67 (s, 2H), 3.76 (s, 3H).

The following nine compounds were prepared by a similar procedure as in Example 40A.

EXAMPLE 40B

2-Amino-3-cyano-4-(4-cyanophenyl)-7-methyl-4H-pyrrolo[2,3-h]chromene $^1$H NMR (CDCl$_3$): 7.58 (d, J=8.2 Hz, 2H), 7.31 (d, J=8.2 Hz, 2H), 7.06 (d, J=2.9 Hz, 1H), 7.03 (d, J=8.4 Hz, 1H), 6.67 (d, J=8.4 Hz, 1H), 6.56 (d, J=3.1 Hz, 1H), 4.91 (s, 1H), 4.73 (s, 2H), 3.78 (s, 3H).

EXAMPLE 40C

2-Amino-3-cyano-4-(3-chlorophenyl)-7-methyl-4H-pyrrolo[2,3-h]chromene $^1$H NMR (CDCl$_3$): 7.25-7.13 (m, 4H), 7.05 (dd, J=2.3 and 0.6 Hz, 1H), 7.02 (d, J=8.6 Hz, 1H), 6.73 (d, J=8.4 Hz, 1H), 6.56 (m, 1H), 4.82 (s, 1H), 4.68 (s, 2H), 3.77 (s, 3H)

EXAMPLE 40D

2-Amino-3-cyano-4-(3,5-dichlorophenyl)-7-methyl-4H-pyrrolo[2,3-h]chromene $^1$H NMR (CDCl$_3$): 7.21-7.20 (m, 1H), 7.09 (t, J=1.6 Hz, 1H), 7.06 (d, J=2.3 Hz, 1H), 7.05 (s, 1H), 7.03 (s, 1H), 6.71 (d, J=8.6 Hz, 1H), 6.57 (d, J=2.3 Hz, 1H), 4,80 (s, 1H), 4.73 (s, 2H), 3.77 (s, 3H).

EXAMPLE 40E

2-Amino-3-cyano-4-(3,4-dichlorophenyl)-7-methyl-4H-pyrrolo[2,3-h]chromene $^1$H NMR (CDCl$_3$): 7.36 (d, J=8.3 Hz, 1H), 7.10-7.02 (m, 4H), 6.70 (d, J=8.8 Hz, 1H), 6.56 (d, J=2.7 Hz, 1H), 4.81 (s, 1H), 4.70 (s, 2H), 3.78 (s, 3H).

EXAMPLE 40F

2-Amino-3-cyano-4-(3-bromo-4,5-dimethoxyphenyl)-7,9-dimethyl-4H-pyrrolo[2,3-h]chromene $^1$H NMR (CDCl$_3$): 6.95 (dd, J=8.6, 1.4 Hz, 1H), 6.91 (m, 1H), 6.78-6.76 (m, 2H), 6.70 (d, J=8.8 Hz, 1H), 4.77 (s, 1H), 4.61 (s, 2H), 3.84 (s, 3H), 3.83 (s, 3H), 3.68 (s, 3H), 2.48 (s, 3H).

EXAMPLE 40G

2-Amino-3-cyano-4-(3,4 difluorophenyl)-7-methyl-4H-pyrrolo[2,3-h]chromene $^1$H NMR (Acetone-$d_6$): 7.31-7.11 (m, 5H), 6.81 (d, J=8.6 Hz, 1H,), 6.51 (d, J=3.1 Hz, 1H), 6.28 (brs, 2H), 4.90 (s, 3H).

EXAMPLE 40H

2-Amino-3-cyano-4-(3-fluoro-4-chlorophenyl)-7-methyl-4H-pyrrolo[2,3-h]chromene $^1$H NMR (Acetone-$d_6$): 7.47 (t, J=8.0 Hz, 1H), 7.26 (d, J=3.1 Hz, 1H), 7.22-7.12 (m, 3H), 6.82 (d, J=8.4 Hz, 1H), 6.51 (dd, J=3.1, 0.6 Hz, 1H), 6.31 (brs, 2H), 4.92 (s, 1H), 3.82 (s, 3H).

EXAMPLE 40I

2-Amino-3-cyano-4-(3-bromo-4-fluorophenyl)-7-methyl-4H-pyrrolo[2,3-h]chromene $^1$H NMR (Acetone-$d_6$): 7.53 (dd, J=2.2, 6.6 Hz, 1H), 7.34-7.30 (m, 1H), 7.27-7.21 (m, 2H), 7.15 (dd, J=0.8, 3.0 Hz, 1H), 6.81 (d, J=8.6 Hz, 1H), 6.51 (dd, J=0.8, 3.0 Hz, 1H), 6.30 (brs, 2H), 4.92 (s, 1H), 3.82 (s, 3H).

EXAMPLE 40J

2-Amino-3-cyano-4-(3-cyano-4-fluorophenyl)-7-methyl-4H-pyrrolo[2,3-h]chromene $^1$H NMR (Acetone-$d_6$): 7.75 (dd, J=2.3, 6.1 Hz, 1H), 7.68-7.64 (m, 1H), 7.39 (t, J=8.8 Hz, 1H), 7.27 (d, J=3.1 Hz, 1H), 7.16 (d, J=8.4 Hz, 1H), 6.81 (d, J=8.4 Hz, 1H), 6.51 (d, J=3.1 Hz, 1H), 6.34 (brs, 1H), 5.01 (s, 1H), 3.82 (2, 3H).

EXAMPLE 41

2-Amino-3-cyano-4-(5-methoxy-pyridin-3-yl)-7-methyl-4H-pyrrolo[2,3-h]chromene

The title compound was prepared from 5-methoxy-pyridine-3-carbaldehyde (70 mg, 0.51 mmol), 4-hydroxy-1-methylindole (75 mg, 0.51 mmol), malononitrile (34 mg, 0.51 mmol) and piperidine (0.05 ml, 0.5 mmol) similar to Example 1e to give 21 mg (12%) of white solids. $^1$H NMR (CDCl$_3$): 8.19-8.15 (m, 2H), 7.07-6.99 (m, 3H), 6.73 (d, J=8.4 Hz, 1H), 6.57 (d, J=3.0 Hz, 1H), 4.89 (s, 1H), 4.75 (brs, 2H), 3.81-3.78 (m, 6H).

EXAMPLE 42

2-Amino-3-cyano-4-(3,5-dichloro-phenyl)-7-isopropyl-4H-pyrrolo [2,3-h]chromene a) 4-Benzyloxy-1-isopropyl-1H-indole: To the solution of 4-benzyloxy-1H-indole (1.0 g, 4.48 mmol) in anhydrous DMF (1.0 ml) was added sodium hydride (0.144 g, 6.00 mmol) and the resulting solution was stirred at room temperature until the solution stopped bubbling, then 2-iodopropane (2.2 g, 60.0 mmol) was added to this solution which was stirred at room temperature for 12 h. The reaction mixture was diluted with water and dichloromethane. The organic layer was separated, dried over anhydrous Na$_2$SO$_4$, filtered and concentrated under reduced pressure to give a clear oil, which was purified by chromatography on silica-gel (ethyl acetate, hexane 2:98 to 5:95 gradient mixture), to give 700 mg (59% yield) of the title compound as a white powder. $^1$H NMR (CDCl$_3$): 7.65-7.00 (m, 8H), 6.70 (s, 1H), 6.60 (d, 1H), 5.25 (s, 2H), 4.65 (m, 1H), 1.51 (s, 6H).

b) 1-Isopropyl-1H-indol-4-ol: To a solution of 4-benzyloxy-1-isopropyl-1H-indole (0.50 g, 1.89 mmol) dissolved in 30 ml of methanol, was added palladium (0.50 g, 5% on carbon) under nitrogen. The mixture was stirred for 4 h under 20 PSI of hydrogen. The reaction mixture was filtered and the resulting solution was concentrated under reduced pressure and the resulting residue was purified by flash chromatography (ethyl acetate 10%/90% hexane) to give 240 mg (73% yield) of the title compound as a beige powder. $^1$H NMR (CDCl$_3$): 7.19 (d, 1H), 7.08 (t, 1H), 7.02 (d, 1H), 6.59 (s, 1H), 6.55 (d, 1H), 5.5-4.7 (bs, 1H), 4.68 (m, 1H), 1.51 (d, 6H).

c) 2-Amino-3-cyano-4-(3,5-dichloro-phenyl)-7-isopropyl-4H-pyrrolo-[2,3-h]chromene: A mixture of 1-isopropyl-1H-indol-4-ol (0.050 g, 0.285 mmol), 3,5-dichloro-benzaldehyde (0.050 g, 0.285 mmol), piperidine (12 uL, 0.14 mmol) and malononitrile (20 mg, 0.30 mmol) in 1.0 ml of ethanol was stirred for 12 h. The mixture was filtered and the solid was washed with ethanol, dried under high vacuum to give 80 mg (70% yield) of the title compound as a white powder. $^1$H NMR (acetone-$d_6$): 7.46 (d, 1H), 7.35 (d, 2H), 7.31 (d, 2H), 7.27 (d, 1H), 6.84 (d, 1H), 6.57 (d, 1H), 6.36 (bs, 2H), 4.95 (s, 1H), 4.75 (m, 1H), 1.51 (d, 6H).

EXAMPLE 43

2-Amino-3-cyano-4-(3-bromo-4,5-dimethoxy-phenyl)-7-isopropyl-4H-pyrrolo[2,3-h]chromene The title compound was prepared by a procedure similar to Example 42 and obtained in 30% yield as a beige powder. $^1$H NMR (acetone-$d_6$): 7.44 (d, 1H), 7.23 (d, 1H), 7.07 (d, 1H), 7.01 (d, 1H), 6.86 (d, 1H), 6.56 (s, 1H), 6.14 (bs, 2H), 4.83 (s, 1H), 4.64 (m, 1H), 3.88 (s, 3H), 3.77 (s, 3H), 1.51 (d, 6H).

EXAMPLE 44

Identification of 2-Amino-4-(5-cyano-pyridin-3-yl)-3-cyano-7-methyl-4H-pyrrolo[2,3-h]chromene and Analogs as Caspase Cascade Activators and Inducers of Apoptosis in Solid Tumor Cells Human breast cancer cell lines T-47D and ZR-75-1 were grown according to media component mixtures designated by American Type Culture Collection+10% FCS (Invitrogen Corporation), in a 5% CO$_2$-95% humidity incubator at 37° C. T-47D and ZR-75-1 cells were maintained at a cell density between 30 and 80% confluency at a cell density of 0.1 to 0.6×10$^6$ cells/mL. Cells were harvested at 600×g and resuspended at 0.65×10$^6$ cells/mL into appropriate media+10% FCS. An aliquot of 45 µl of cells was added to a well of a 96-well microtiter plate containing 5 µl of a 10% DMSO in RPMI-1640 media solution containing about 0.16 to 10 µM of 2-amino-3-cyano-4-(5-methyl-pyridin-3-yl)-7-methyl-4H-pyrrolo[2,3-h]chromene (Example 10) or other test compound (0.016 to 1 µM final). An aliquot of 45 µl of cells was added to a well of a 96-well microtiter plate containing 5 µl of a 10% DMSO in RPMI-1640 media solution without test compound as the control sample. The samples were mixed by agitation and then incubated at 37° C. for 24 h in a 5% CO$_2$-95% humidity incubator. After incubation, the samples were removed from the incubator and 50 µl of a solution containing 20 µM of N-(Ac-DEVD)-N'-ethoxycarbonyl-R110 (SEQ ID No:1) fluorogenic substrate (Cytovia, Inc.; U.S. Pat. No. 6,335,429), 20% sucrose (Sigma), 20 mM DTT (Sigma), 200 mM NaCl (Sigma), 40 mM Na PIPES buffer pH 7.2 (Sigma), and 500 µg/ml lysolecithin (Calbiochem) was added. The samples were mixed by agitation and incubated at room temperature. Using a fluorescent plate reader (Model 1420 Wallac Instruments), an initial reading (T=0) was made approximately 1-2 min after addition of the substrate solution, employing excitation at 485 nm and emission at 530 nm, to determine the background fluorescence of the control sample. After the 3 h incubation, the samples were read for fluorescence as above (T=3 h).

Calculation:

The Relative Fluorescence Unit values (RFU) were used to calculate the sample readings as follows:

$$RFU_{(T=3h)} - \text{Control } RFU_{(T=0)} = \text{Net } RFU_{(T=3h)}$$

The activity of caspase cascade activation was determined by the ratio of the net RFU value for 2-amino-3-cyano-4-(5-methyl-pyridin-3-yl)-7-methyl-4H-pyrrolo[2,3-h]chromene or other test compound to that of control samples. The $EC_{50}$ (nM) was determined by a sigmoidal dose-response calculation (Prism 2.0, GraphPad Software Inc.). The caspase activity (Ratio) and potency ($EC_{50}$) are summarized in Table I:

TABLE I

| | Caspase Activity and Potency | | | |
|---|---|---|---|---|
| | T-47D | | ZR-75-1 | |
| Example # | Ratio | $EC_{50}$ (nM) | Ratio | $EC_{50}$ (nM) |
| 1 | 8.3 | 25.5 | 5.2 | 6.5 |
| 2 | 8.2 | 110.1 | 4.3 | 41.3 |
| 3 | 5.6 | 58.1 | 3.1 | 27.8 |
| 4 | 6.6 | 14.0 | 9.2 | 13.1 |
| 5 | 4.0 | 55.3 | 3.0 | 28.6 |
| 6 | 3.3 | 413.4 | 7.0 | 258.9 |
| 7 | 5.1 | 6.7 | 13.1 | 2.7 |
| 8 | 3.8 | 58.7 | 8.9 | 55.0 |
| 9 | 8.3 | 14.2 | 7.8 | 6.2 |
| 10 | 3.1 | 2.3 | 6.6 | 1.6 |
| 11 | 4.6 | 2.9 | 4.1 | 1.1 |
| 12 | 5.4 | 1.6 | 8.5 | 1.5 |
| 13 | 8.8 | 6.8 | 8.0 | 3.2 |
| 14 | 8.0 | 19.8 | 9.9 | 10.4 |
| 16 | 8.1 | 1.6 | 11.7 | 1.0 |
| 17 | 7.2 | 2.1 | 3.3 | 1.6 |
| 18 | 4.0 | 6.0 | 6.6 | 3.4 |
| 19 | 10.2 | 231.0 | 11.7 | 106.8 |
| 20 | 4.7 | 3.7 | 6.3 | 2.4 |
| 21 | 2.2 | 3.0 | 4.4 | 1.6 |
| 22 | 5.3 | 3.4 | 7.2 | 2.0 |
| 23 | 5.2 | 3.3 | 5.0 | 2.3 |
| 24 | 5.5 | 3.4 | 7.1 | 2.2 |
| 25 | 3.2 | 7.2 | 7.1 | 3.2 |
| 26 | 5.2 | 3.5 | 7.1 | 1.7 |
| 27 | 4.1 | 14 | 5.8 | 7.1 |
| 28 | 4.6 | 7.2 | 6.3 | 3.3 |
| 29 | 3.3 | 12 | 6.3 | 5.7 |
| 30 | 3.6 | 7.3 | 5.6 | 3.4 |
| 31 | 6.3 | 4.9 | 4.3 | 3.7 |
| 32 | 5.3 | 6.9 | 3.6 | 2.9 |
| 33 | 4.3 | 6.2 | 3.0 | 3.3 |
| 34 | 3.3 | 7.1 | 3.9 | 6.5 |
| 35 | 4.3 | 28 | 5.5 | 10 |
| 36 | 4.6 | 13 | 6.3 | 5 |
| 37 | 2.0 | >100 | 6.7 | 36 |
| 38 | 5.2 | 55 | 6.9 | 29 |
| 39 | 3.7 | 51 | 6.2 | 26 |
| 40A | 5.1 | 14 | 4.1 | 7.2 |
| 40B | 4.9 | 55 | 4.2 | 35 |
| 40C | 4.0 | 14 | 2.7 | 7.9 |
| 40D | 3.3 | 25 | 2.9 | 15 |
| 40E | 1.3 | >100 | 3.2 | 81 |
| 40F | 2.6 | 42 | 3.9 | 26 |
| 40G | 4.6 | 29 | 5.9 | 15 |
| 40H | 1.3 | >100 | 6.0 | 56 |
| 40I | 3.9 | 29 | 4.4 | 14 |
| 40J | 3.6 | 29 | 5.8 | 14 |
| 41 | 3.8 | 4 | 4.2 | 2 |
| 42 | 1.8 | >100 | 2.6 | 57 |
| 43 | 2.5 | 58 | 6.3 | 55 |

Thus, 2-Amino-3-cyano-4-(5-methyl-pyridin-3-yl)-7-methyl-4H-pyrrolo[2,3-h]chromene (Example 10) and analogs are identified as potent caspase cascade activators and inducers of apoptosis in solid tumor cells.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A compound of formula I:

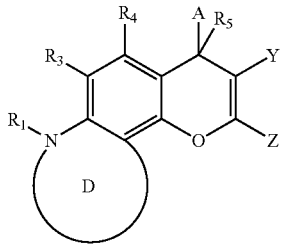

wherein, $R_1$ is methyl, hydroxymethyl, or an ester of said hydroxymethyl;

$R_3$ and $R_4$ are independently hydrogen, halo, haloalkyl, $C_{1-10}$ alkyl, alkenyl, alkynyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol;

$R_5$ is hydrogen or $C_{1-10}$ alkyl;

A is an optionally substituted phenyl or pyridyl, wherein said optional substituent is one or more of hydrogen, halo, haloalkyl, $C_{1-10}$ alkyl, alkenyl, alkynyl, hydroxyalkyl, aminoalkyl, carboxyalkyl, nitro, amino, cyano, acylamido, hydroxy, thiol, acyloxy, azido, alkoxy, carboxy, methylenedioxy, ethylenedioxy, carbonylamido or alkylthiol;

D together with the rings to which it is fused is 4H-pyrrolo[2,3-h]chromene;

Y is CN; and

Z is $NR_{22}R_{23}$, wherein $R_{22}$ and $R_{23}$ are independently H or $C_{1-4}$ alkyl;

or a pharmaceutically acceptable salt thereof.

2. The compound of claim 1, wherein each of $R_3$-$R_5$ is hydrogen.

3. The compound of claim 1, wherein Z is $NH_2$.

4. The compound of claim 1, wherein:

$R_1$ is methyl, hydroxymethyl or an ester of said hydroxymethyl;

$R_3$ and $R_4$ are independently hydrogen or methyl;

A is an optionally substituted phenyl, wherein said optional substituents are independently selected from the group consisting of hydrogen, hydroxy, halogen, cyano, alkoxy and acetoxy or combines with another of the optional substituents to form methylenedioxy or ethylenedioxy;

Y is cyano; and

Z is $NR_{22}R_{23}$, wherein $R_{22}$ and $R_{23}$ are independently H or $C_{1-4}$ alkyl.

5. The compound of claim 4, wherein said compound is selected from the group consisting of:

2-Amino-4-(3-bromo-4,5-dimethoxyphenyl)-3-cyano-7-methyl-4H-pyrrolo [2,3-h]chromene;

2-Amino-4-(3-bromo-4,5-dimethoxyphenyl)-3-cyano-7-hydroxymethyl-4H-pyrrolo [2,3-h]chromene;

2-Amino-4-(3-bromo-4-hydroxy-5-methoxyphenyl)-3-cyano-7-methyl-4H-pyrrolo [2,3-h]chromene;

2-Amino-4-(4-acetoxy-3-bromo-5-methoxyphenyl)-3-cyano-7-methyl-4H-pyrrolo [2,3-h]chromene;

2-Amino-3-cyano-4-(3,4,5-trimethoxyphenyl)-7-methyl-4H-pyrrolo [2,3-h]chromene;

2-Amino-3-cyano-4-(3-nitrophenyl)-7-methyl-4H-pyrrolo[2,3-h]chromene;

2-Amino-3-cyano-4-(3,5-dimethoxyphenyl)-7-methyl-4H-pyrrolo [2,3-h]chromene;

2-Amino-3-cyano-4-(3,4-methylenedioxo-5-methoxyphenyl)-7-methyl-4H-pyrrolo [2,3-h]chromene;

2-Amino-3-cyano-4-(3-methoxyphenyl)-7-methyl-4H-pyrrolo[2,3-h]chromene;

2-Amino-3-cyano-4-(3-bromophenyl)-7-methyl-4H-pyrrolo[2,3-h]chromene;

2-Amino-3-cyano-4-(3,5-difluorophenyl)-7-methyl-4H-pyrrolo[2,3-h]chromene;

2-Amino-3-cyano-4-(4,5-dimethoxy-3-iodophenyl)-7-methyl-4H-pyrrolo [2,3-h]chromene;

2-Amino-3-cyano-4-(3-cyanophenyl)-7-methyl-4H-pyrrolo[2,3-h]chromene;

2-Amino-3-cyano-4-(3,4,5-trimethoxyphenyl)-7-hydroxymethyl-4H-pyrrolo [2,3-h]chromene;

2-Amino-3-cyano-4-(3,5-dimethoxyphenyl)-7-hydroxymethyl-4H-pyrrolo [2,3-h]chromene;

4,7,10,13,16,19-Docosahexaenoic acid {2-Amino-4-(3-bromo-4,5-dimethoxyphenyl)-3-cyano-4H-pyrrolo [2,3-h]chromene}-7-ylmethyl ester;

2-Amino-3-cyano-4-(3-fluorophenyl)-7-methyl-4H-pyrrolo[2,3-h]chromene;

2-Amino-3-cyano-4-(4-cyanophenyl)-7-methyl-4H-pyrrolo[2,3-h]chromene;

2-Amino-3-cyano-4-(3-chlorophenyl)-7-methyl-4H-pyrrolo[2,3-h]chromene;

2-Amino-3-cyano-4-(3,5-dichlorophenyl)-7-methyl-4H-pyrrolo[2,3-h]chromene;

2-Amino-3-cyano-4-(3,4-dichlorophenyl)-7-methyl-4H-pyrrolo[2,3-h]chromene;

2-Amino-3-cyano-4-(3,4-difluorophenyl)-7-methyl-4H-pyrrolo[2,3-h]chromene;

2-Amino-3-cyano-4-(3-fluoro-4-chlorophenyl)-7-methyl-4H-pyrrolo [2,3-h]chromene;

2-Amino-3-cyano-4-(3-bromo-4-fluorophenyl)-7-methyl-4H-pyrrolo [2,3-h]chromene; and 2-Amino-3-cyano-4-(3-cyano-4-fluorophenyl)-7-methyl-4H-pyrrolo [2,3-h]chromene;

or a pharmaceutically acceptable salt thereof.

6. The compound of claim 1, wherein:

$R_1$ is methyl, hydroxymethyl or an ester of said hydroxymethyl;

$R_3$ and $R_4$ are independently hydrogen or methyl;

A is an optionally substituted pyridyl, wherein said optional substituents are independently selected from the group consisting of hydrogen, hydroxy, halogen, cyano, alkoxy and acetoxy or combines with another of the optional substituents to form methylenedioxy or ethylenedioxy;

Y is cyano; and

Z is $NR_{22}R_{23}$, wherein $R_{22}$ and $R_{23}$ are independently H or $C_{1-4}$ alkyl.

7. The compound of claim 6, wherein said compound is selected from the group consisting of:

2-Amino-4-(5-cyano-pyridin-3-yl)-3-cyano-7-methyl-4H-pyrrolo [2,3-h]chromene;

2-Amino-4-(5-chloro-pyridin-3-yl)-3-cyano-7-methyl-4H-pyrrolo [2,3-h]chromene;

2-Amino-4-(5-chloro-6-hydroxy-pyridin-3-yl)-3-cyano-7-methyl-4H-pyrrolo [2,3-h]chromene;

2-Amino-3-cyano-4-(5-methyl-pyridin-3-yl)-7-methyl-4H-pyrrolo [2,3-h]chromene;

2-Amino-4-(5-bromo-pyridin-3-yl)-3-cyano-7-methyl-4H-pyrrolo [2,3-h]chromene;

2-Amino-3-cyano-4-(5-methyl-pyridin-3-yl)-7-hydroxymethyl-4H-pyrrolo [2,3-h]chromene;
2-Amino-4-(5-bromo-pyridin-3-yl)-3-cyano-7-hydroxymethyl-4H-pyrrolo [2,3-h]chromene;
2-Amino-3-cyano-4-(5-methoxy-pyridin-3-yl)-7-methyl-4H-pyrrolo [2,3-h]chromene; and
4,7,10,13,16,19-Docosahexaenoic acid {2-Amino-3-cyano-4-(5-methyl-pyridin-3-yl)-4H-pyrrolo [2,3-h]chromene}-7-ylmethyl ester;
or a pharmaceutically acceptable salt thereof.

8. A pharmaceutical composition comprising the compound of claim 1, or a pharmaceutically acceptable salt thereof, and a pharmaceutically acceptable excipient or carrier.

9. The pharmaceutical composition of claim 8, wherein said excipient or carrier is selected from the group consisting of saccharides, starch pastes, gelatin, tragacanth, cellulose preparations, calcium phosphates and polyvinyl pyrrolidone.

10. The pharmaceutical composition of claim 9, wherein said excipient or carrier is a saccharide selected from the group consisting of lactose, sucrose, mannitol and sorbitol.

11. The pharmaceutical composition of claim 8, wherein said excipient or carrier is a lipophilic solvent.

12. The pharmaceutical composition of claim 11, wherein said lipophilic solvent is selected from the group consisting of fatty oils, fatty acid esters, polyethylene glycols and paraffin hydrocarbons.

13. The pharmaceutical composition of claim 11, wherein said lipophilic solvent is selected from the group consisting of sesame oil, ethyl oleate, triglycerides, polyethylene glycol-400, cremophor and cyclodextrins.

14. The pharmaceutical composition of claim 8, wherein said excipient or carrier is selected from the group consisting of vegetable oils, mineral oils, white petrolatum, branched chain fats, branched chain oils, animal fats and high molecular weight alcohol (greater than $C_{12}$).

15. The pharmaceutical composition of claim 8, wherein said excipient or carrier is a saline solution.

16. The pharmaceutical composition of claim 8, wherein said compound is selected from the group consisting of:
2-Amino-4-(5-cyano-pyridin-3-yl)-3-cyano-7-methyl-4H-pyrrolo [2,3-h]chromene;
2-Amino-4-(5-chloro-pyridin-3-yl)-3-cyano-7-methyl-4H-pyrrolo [2,3-h]chromene;
2-Amino-4-(5-chloro-6-hydroxy-pyridin-3-yl)-3-cyano-7-methyl-4H-pyrrolo [2,3-h]chromene;
2-Amino-3-cyano-4-(5-methyl-pyridin-3-yl)-7-methyl-4H-pyrrolo [2,3-h]chromene;
2-Amino-4-(5-bromo-pyridin-3-yl)-3-cyano-7-methyl-4H-pyrrolo [2,3-h]chromene;
2-Amino-4-(3-bromo-4,5-dimethoxyphenyl)-3-cyano-7-methyl-4H-imidazo [4,5-h]chromene;
2-Amino-4-(5-bromo-pyridin-3-yl)-3-cyano-7-methyl-4H-imidazo [4,5-h]chromene;
2-Amino-3-cyano-4-(5-methyl-pyridin-3-yl)-7-methyl-4H-imidazo [4,5-h]chromene;
2-Amino-4-(3-bromo-4,5-dimethoxyphenyl)-3-cyano-7-methyl-4H-pyrrolo [2,3-h]chromene;
2-Amino-4-(3-bromo-4,5-dimethoxyphenyl)-3-cyano-7-hydroxymethyl-4H-pyrrolo [2,3-h]chromene;
2-Amino-4-(3-bromo-4-hydroxy-5-methoxyphenyl)-3-cyano-7-methyl-4H-pyrrolo [2,3-h]chromene;
2-Amino-3-cyano-4-(5-methyl-pyridin-3-yl)-7-hydroxymethyl-4H-pyrrolo [2,3-h]chromene;
2-Amino-4-(5-bromo-pyridin-3-yl)-3-cyano-7-hydroxymethyl-4H-pyrrolo[2,3-h]chromene;
2-Amino-4-(4-acetoxy-3-bromo-5-methoxyphenyl)-3-cyano-7-methyl-4H-pyrrolo [2,3-h]chromene;
2-Amino-4-(3-bromo-4,5-dimethoxyphenyl)-3-cyano-8,9-dihydro-7-methyl-4H-pyrrolo [2,3-h]chromene;
2-Amino-3-cyano-4-(3,4,5-trimethoxyphenyl)-7-methyl-4H-pyrrolo [2,3-h]chromene;
2-Amino-3-cyano-4-(3-nitrophenyl)-7-methyl-4H-pyrrolo [2,3-h]chromene;
2-Amino-3-cyano-4-(3,5-dimethoxyphenyl)-7-methyl-4H-pyrrolo [2,3-h]chromene;
2-Amino-3-cyano-4-(3,4-methylenedioxo-5-methoxyphenyl)-7-methyl-4H-pyrrolo [2,3-h]chromene;
2-Amino-3-cyano-4-(3-methoxyphenyl)-7-methyl-4H-pyrrolo [2,3-h]chromene;
2-Amino-3-cyano-4-(3-bromophenyl)-7-methyl-4H-pyrrolo[2,3-h]chromene;
2-Amino-3-cyano-4-(3,5-difluorophenyl)-7-methyl-4H-pyrrolo [2,3-h]chromene;
2-Amino-3-cyano-4-(4,5-dimethoxy-3-iodophenyl)-7-methyl-4H-pyrrolo [2,3-h]chromene;
2-Amino-3-cyano-4-(3-cyanophenyl)-7-methyl-4H-pyrrolo [2,3-h]chromene;
2-Amino-3-cyano-4-(3,4,5-trimethoxyphenyl)-7-hydroxymethyl-4H-pyrrolo [2,3-h]chromene;
2-Amino-3-cyano-4-(3,5-dimethoxyphenyl)-7-hydroxymethyl-4H-pyrrolo [2,3-h]chromene;
2-Amino-3-cyano-4-(3,5-difluorophenyl)-8,9-dihydro-7-methyl-4H-pyrrolo [2,3-h]chromene;
2-Amino-4-(5-methyl-pyridin-3-yl)-3-cyano-7-methyl-8,9-dihydro-4H-pyrrolo [2,3-h]chromene;
4,7,10,13,16,19-Docosahexaenoic acid {2-Amino-4-(3-bromo-4,5-dimethoxyphenyl)-3-cyano-4H-pyrrolo [2,3-h]chromene}-7-ylmethyl ester;
4,7,10,13,16,19-Docosahexaenoic acid {2-Amino-3-cyano-4-(5-methyl-pyridin-13-yl-) 4H-pyrrolo [2,3-h] chromene }-7-ylmethyl ester;
2-Amino-3-cyano-4-(3-fluorophenyl)-7-methyl-4H-pyrrolo[2,3-h]chromene;
2-Amino-3-cyano-4-(4-cyanophenyl)-7-methyl-4H-pyrrolo[2,3-h]chromene;
2-Amino-3-cyano-4-(3-chlorophenyl)-7-methyl-4H-pyrrolo[2,3-h]chromene;
2-Amino-3-cyano-4-(3,5-dichlorophenyl)-7-methyl-4H-pyrrolo[2,3-h]chromene;
2-Amino-3-cyano-4-(3,4-dichlorophenyl)-7-methyl-4H-pyrrolo[2,3-h]chromene;
2-Amino-3-cyano-4-(3-bromo-4,5-dimethoxyphenyl)-7,9-dimethyl-4H-pyrrolo [2,3-h]chromene;
2-Amino-3-cyano-4-(3,4-difluorophenyl)-7-methyl-4H-pyrrolo[2,3-h]chromene;
2-Amino-3-cyano-4-(3-fluoro-4-chlorophenyl)-7-methyl-4H-pyrrolo [2,3-h]chromene;
2-Amino-3-cyano-4-(3-bromo-4-fluorophenyl)-7-methyl-4H-pyrrolo [2,3-h]chromene; and
2-Amino-3-cyano-4-(3-cyano-4-fluorophenyl)-7-methyl-4H-pyrrolo [2,3-h]chromene; and
2-Amino-3-cyano-4-(5-methoxy-pyridin-3-yl)-7-methyl-4H-pyrrolo [2,3-h]chromene;
or a pharmaceutically acceptable salt thereof.

17. The compound of claim 1, wherein $R_1$ is methyl.
18. The compound of claim 1, wherein $R_1$ is hydroxymethyl.
19. The composition of claim 8, wherein $R_1$ is methyl.
20. The composition of claim 8, wherein $R_1$ is hydroxymethyl.
21. The compound of claim 1, wherein said ester of said hydroxymethyl is obtained by condensation of the hydroxymethyl group with a $C_{1-40}$ carboxylic acid or with a $C_{3-6}$ dioic acid or anhydride thereof.

22. The composition of claim 8, wherein said ester of said hydroxymethyl is obtained by condensation of the hydroxymethyl group with a $C_{1-40}$ carboxylic acid or with a $C_{3-6}$ dioic acid or anhydride thereof.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: N-terminal acetyl
<220> FEATURE:
<221> NAME/KEY: MOD_RES
<222> LOCATION: (4)..(4)
<223> OTHER INFORMATION: C-terminal N'-ethoxycarbonyl-Rhodamine 110

<400> SEQUENCE: 1

Asp Glu Val Asp
1
```